(12) United States Patent
McDaniel

(10) Patent No.: US 8,651,112 B2
(45) Date of Patent: Feb. 18, 2014

(54) PROCESS FOR TREATMENT OF PSORIASIS

(76) Inventor: David McDaniel, Virginia Beach, VA (US)

( * ) Notice: Subject to any disclaimer, the term of this patent is extended or adjusted under 35 U.S.C. 154(b) by 0 days.

(21) Appl. No.: 12/753,207

(22) Filed: Apr. 2, 2010

(65) Prior Publication Data

US 2010/0256550 A1 Oct. 7, 2010

Related U.S. Application Data

(60) Continuation of application No. 09/819,083, filed on Feb. 15, 2001, now abandoned, which is a division of application No. 09/203,178, filed on Nov. 30, 1998, now Pat. No. 6,283,956.

(51) Int. Cl.
*A61B 19/00* (2006.01)
*A61N 5/06* (2006.01)

(52) U.S. Cl.
USPC .............................. 128/898; 607/88

(58) Field of Classification Search
USPC ............ 607/88–91, 100, 101; 606/9, 10, 127, 606/131, 133; 128/898
See application file for complete search history.

(56) References Cited

U.S. PATENT DOCUMENTS

| | | | |
|---|---|---|---|
| 3,499,437 A | 3/1970 | Balamuth | |
| 3,876,907 A | 4/1975 | Widmayer | |
| 3,930,335 A | 1/1976 | Widmayer | |
| 4,069,823 A | 1/1978 | Isakov et al. | |
| 4,309,989 A | 1/1982 | Fahim | |
| 4,558,700 A * | 12/1985 | Mutzhas | 607/94 |
| 4,603,496 A | 8/1986 | Latz et al. | |
| 4,621,287 A | 11/1986 | Reitmeier et al. | |
| 4,628,422 A | 12/1986 | Ewald | |
| 4,646,743 A | 3/1987 | Parris | |
| 4,753,958 A | 6/1988 | Weinstein et al. | |
| 4,764,379 A | 8/1988 | Sanders et al. | |
| 4,767,402 A | 8/1988 | Kost et al. | |
| 4,781,924 A | 11/1988 | Lee et al. | |
| 4,822,335 A | 4/1989 | Kawai et al. | |
| 4,836,203 A | 6/1989 | Muller et al. | |
| 4,837,027 A | 6/1989 | Lee et al. | |
| 4,880,001 A | 11/1989 | Weinberg | |
| 4,888,354 A | 12/1989 | Chang et al. | |
| 4,907,132 A | 3/1990 | Parker | |
| 4,930,504 A | 6/1990 | Diamantopoulos et al. | |
| 4,932,934 A | 6/1990 | Dougherty et al. | |
| 4,935,665 A | 6/1990 | Murata | |
| 4,969,912 A | 11/1990 | Kelman et al. | |
| 5,001,556 A | 3/1991 | Nakamura et al. | |
| 5,012,609 A | 5/1991 | Ignatius et al. | |
| 5,016,615 A | 5/1991 | Driller et al. | |
| 5,021,452 A | 6/1991 | Labbe et al. | |
| 5,034,613 A | 7/1991 | Denk et al. | |
| 5,037,432 A | 8/1991 | Molinari | |
| 5,071,416 A | 12/1991 | Heller et al. | |
| 5,147,349 A | 9/1992 | Johnson et al. | |
| 5,150,704 A | 9/1992 | Tatebayashi et al. | |
| 5,171,215 A | 12/1992 | Flanagan | |
| 5,198,465 A | 3/1993 | Dioguardi | |
| 5,226,907 A | 7/1993 | Tankovich | |
| 5,231,975 A | 8/1993 | Bommannan et al. | |
| 5,257,173 A | 10/1993 | Ohmamyuda et al. | |
| 5,259,380 A | 11/1993 | Mendes et al. | |
| 5,262,401 A | 11/1993 | Vogel et al. | |
| 5,266,480 A | 11/1993 | Naughton et al. | |
| 5,278,432 A | 1/1994 | Ignatius et al. | |
| 5,332,802 A | 7/1994 | Kelman et al. | |
| 5,344,434 A | 9/1994 | Talmore | |
| 5,358,503 A | 10/1994 | Bertwell et al. | |
| 5,360,824 A | 11/1994 | Barker | |
| 5,366,498 A | 11/1994 | Brannan et al. | |
| 5,397,352 A | 3/1995 | Burres | |
| 5,399,583 A | 3/1995 | Levy et al. | |
| 5,421,816 A | 6/1995 | Lipkovker | |
| 5,423,803 A | 6/1995 | Tankovich et al. | |
| 5,425,728 A | 6/1995 | Tankovich | |

(Continued)

FOREIGN PATENT DOCUMENTS

| | | |
|---|---|---|
| EP | 0159446 | 10/1985 |
| EP | 0298661 | 1/1989 |

(Continued)

OTHER PUBLICATIONS

Westerhof et al. "Treatment of Vitiligo with UV-B Radiation vs Topical Psoralen Plus UV-A," Arch Dermatol, vol. 133, Dec. 1997, pp. 1525-1528.*

(Continued)

*Primary Examiner* — Ahmed Farah

(74) *Attorney, Agent, or Firm* — Nelson Mullins Riley & Scarborough LLP

(57) ABSTRACT

A system for producing preferential damage to hair exiting mammalian skin. A agent having an average diameter for enabling the agent to penetrate the hair duct is selected. The agent is designed to attach to, or become physically incorporated into, the hair shaft, the hair follicle, the hair bulb or the hair duct. The agent has an electromagnetic radiation absorption characteristic which enables the agent to absorb a first wavelength of electromagnetic radiation from a skin-penetrating electromagnetic radiation source, such as a laser. The agent is applied to the skin so that the agent penetrates the skin and attaches to or becomes physically incorporated into the hair shaft, the hair follicle, the hair bulb or the hair duct. The agent is exposed to the first wavelength of electromagnetic radiation and absorbs the first wavelength of electromagnetic radiation.

6 Claims, 5 Drawing Sheets

(56) References Cited

U.S. PATENT DOCUMENTS

| | | |
|---|---|---|
| 5,445,146 A | 8/1995 | Bellinger |
| 5,445,608 A | 8/1995 | Chen et al. |
| 5,445,611 A | 8/1995 | Eppstein et al. |
| 5,445,634 A | 8/1995 | Keller |
| 5,460,939 A | 10/1995 | Hansbrough et al. |
| 5,474,528 A | 12/1995 | Meserol |
| 5,492,135 A | 2/1996 | Devore |
| 5,500,009 A | 3/1996 | Mendes et al. |
| 5,549,660 A | 8/1996 | Mendes et al. |
| 5,591,444 A | 1/1997 | Boss, Jr. |
| 5,616,140 A | 4/1997 | Prescott |
| 5,618,275 A | 4/1997 | Bock |
| 5,620,478 A | 4/1997 | Eckhouse |
| 5,634,711 A | 6/1997 | Kennedy et al. |
| 5,636,632 A | 6/1997 | Bommannan et al. |
| 5,643,334 A | 7/1997 | Eckhouse et al. |
| 5,647,866 A | 7/1997 | Zaias et al. |
| 5,658,323 A | 8/1997 | Miller |
| 5,660,461 A | 8/1997 | Ignatius et al. |
| 5,660,836 A | 8/1997 | Knowlton |
| 5,660,850 A | 8/1997 | Boss, Jr. |
| 5,662,644 A | 9/1997 | Swor |
| 5,665,053 A | 9/1997 | Jacobs |
| 5,665,372 A | 9/1997 | Boss, Jr. |
| 5,669,916 A | 9/1997 | Anderson |
| 5,683,380 A | 11/1997 | Eckhouse et al. |
| 5,698,866 A * | 12/1997 | Doiron et al. ............... 257/99 |
| 5,707,401 A | 1/1998 | Talmore |
| 5,728,090 A | 3/1998 | Martin et al. |
| 5,752,948 A | 5/1998 | Tankovich et al. |
| 5,752,949 A | 5/1998 | Tankovich et al. |
| 5,755,752 A | 5/1998 | Segal |
| 5,766,214 A | 6/1998 | Mehl, Sr. et al. |
| 5,766,233 A | 6/1998 | Thiberg |
| 5,766,234 A | 6/1998 | Chen et al. |
| 5,773,609 A | 6/1998 | Robinson et al. |
| 5,800,478 A | 9/1998 | Chen et al. |
| 5,800,479 A | 9/1998 | Thiberg |
| 5,814,599 A | 9/1998 | Mitragotri et al. |
| 5,817,089 A * | 10/1998 | Tankovich et al. ............... 606/9 |
| 5,829,448 A | 11/1998 | Fisher et al. |
| 5,836,999 A | 11/1998 | Eckhouse et al. |
| 5,837,224 A | 11/1998 | Voorhees et al. |
| 5,843,072 A | 12/1998 | Furumoto et al. |
| 5,849,029 A | 12/1998 | Eckhouse et al. |
| 5,871,480 A | 2/1999 | Tankovich |
| 5,904,659 A | 5/1999 | Duarte et al. |
| 5,913,883 A | 6/1999 | Alexander et al. |
| 5,932,240 A | 8/1999 | D'Angelo et al. |
| 5,947,921 A | 9/1999 | Johnson et al. |
| 5,951,596 A | 9/1999 | Bellinger |
| 5,954,675 A | 9/1999 | Dellagatta |
| 5,968,034 A | 10/1999 | Fullmer et al. |
| 5,997,569 A | 12/1999 | Chen et al. |
| 6,024,717 A | 2/2000 | Ball et al. |
| 6,030,374 A | 2/2000 | McDaniel |
| 6,048,301 A | 4/2000 | Sabuda |
| 6,050,990 A | 4/2000 | Tankovich et al. |
| 6,063,108 A | 5/2000 | Salansky |
| 6,074,382 A | 6/2000 | Asah et al. |
| 6,096,066 A | 8/2000 | Chen |
| 6,099,522 A | 8/2000 | Knopp |
| 6,110,106 A | 8/2000 | MacKinnon et al. |
| 6,113,559 A | 9/2000 | Klopotek |
| 6,120,497 A | 9/2000 | Anderson et al. |
| 6,130,254 A | 10/2000 | Fisher et al. |
| 6,143,287 A | 11/2000 | Ben-Hur et al. |
| 6,162,211 A | 12/2000 | Tankovich et al. |
| 6,171,331 B1 | 1/2001 | Bagraev et al. |
| 6,171,332 B1 | 1/2001 | Whitehurst |
| 6,174,325 B1 | 1/2001 | Eckhouse |
| 6,183,773 B1 | 2/2001 | Anderson |
| 6,187,029 B1 | 2/2001 | Shapiro et al. |
| 6,190,315 B1 | 2/2001 | Kost et al. |
| 6,190,376 B1 | 2/2001 | Asah |
| 6,214,034 B1 | 4/2001 | Azar |
| 6,221,095 B1 | 4/2001 | Van Zuylen et al. |
| 6,223,071 B1 | 4/2001 | Lundahl et al. |
| 6,231,528 B1 | 5/2001 | Kaufman et al. |
| 6,238,424 B1 | 5/2001 | Thiberg |
| 6,251,127 B1 | 6/2001 | Biel |
| 6,267,779 B1 | 7/2001 | Gerdes |
| 6,273,884 B1 | 8/2001 | Altshuler |
| 6,283,956 B1 | 9/2001 | McDaniel |
| 6,290,713 B1 | 9/2001 | Russell |
| 6,302,874 B1 | 10/2001 | Zhang et al. |
| 6,312,450 B1 | 11/2001 | Yavitz et al. |
| 6,387,089 B1 | 5/2002 | Kreindel et al. |
| 6,398,753 B2 | 6/2002 | McDaniel |
| 6,413,268 B1 | 7/2002 | Hartman |
| 6,436,127 B1 * | 8/2002 | Anderson et al. ............... 607/89 |
| 6,443,946 B2 | 9/2002 | Clement et al. |
| 6,443,978 B1 | 9/2002 | Zharov |
| 6,459,087 B1 | 10/2002 | Kaas |
| 6,471,716 B1 | 10/2002 | Pecukonis |
| 6,497,719 B2 | 12/2002 | Pearl et al. |
| 6,524,330 B1 | 2/2003 | Khoobehi et al. |
| 6,602,275 B1 | 8/2003 | Sullivan |
| 6,629,971 B2 | 10/2003 | McDaniel |
| 6,630,516 B2 | 10/2003 | Varani et al. |
| 6,645,230 B2 | 11/2003 | Whitehurst |
| 6,663,659 B2 | 12/2003 | McDaniel |
| 6,664,217 B1 | 12/2003 | Puvvada et al. |
| 6,676,655 B2 | 1/2004 | McDaniel |
| 6,709,866 B2 | 3/2004 | Robertson et al. |
| 6,723,698 B2 | 4/2004 | Rueger et al. |
| 6,723,798 B1 | 4/2004 | Yoo |
| 6,746,444 B2 | 6/2004 | Key |
| 6,835,306 B2 | 12/2004 | Caldwell |
| 6,866,678 B2 | 3/2005 | Shenderova |
| 6,881,212 B1 | 4/2005 | Clement et al. |
| 6,887,260 B1 | 5/2005 | McDaniel |
| 6,936,044 B2 | 8/2005 | McDaniel |
| 7,004,933 B2 | 2/2006 | McDaniel |
| 7,033,381 B1 | 4/2006 | Larsen |
| 7,081,128 B2 | 7/2006 | Hart et al. |
| 7,115,120 B2 | 10/2006 | Lin |
| 7,147,863 B2 | 12/2006 | Fisher |
| 7,195,755 B2 | 3/2007 | Nguyen et al. |
| 7,201,765 B2 | 4/2007 | McDaniel |
| 7,204,832 B2 | 4/2007 | Altshuler et al. |
| 7,258,695 B2 | 8/2007 | Carullo, Jr. et al. |
| 7,264,629 B2 | 9/2007 | Simkin et al. |
| 7,267,673 B2 | 9/2007 | Pilcher et al. |
| 7,309,335 B2 | 12/2007 | Altshuler et al. |
| 7,331,952 B2 | 2/2008 | Walneck et al. |
| 7,354,432 B2 | 4/2008 | Eells et al. |
| 7,438,719 B2 | 10/2008 | Chung et al. |
| 7,470,270 B2 | 12/2008 | Azar et al. |
| 7,494,503 B2 | 2/2009 | McDaniel |
| 7,511,031 B2 | 3/2009 | Chen |
| 7,559,944 B2 | 7/2009 | Whang |
| 7,597,708 B2 | 10/2009 | Carullo, Jr. et al. |
| 7,618,414 B2 | 11/2009 | Connors et al. |
| 8,188,074 B2 | 5/2012 | Brown et al. |
| 8,372,433 B2 | 2/2013 | Shinoka et al. |
| 2001/0013349 A1 | 8/2001 | Clement |
| 2001/0023363 A1 | 9/2001 | Harth et al. |
| 2001/0053347 A1 | 12/2001 | Varani et al. |
| 2002/0028185 A1 | 3/2002 | Fisher et al. |
| 2002/0029071 A1 | 3/2002 | Whitehurst |
| 2002/0123746 A1 | 9/2002 | McDaniel |
| 2002/0161357 A1 | 10/2002 | Anderson et al. |
| 2002/0173833 A1 | 11/2002 | Korman et al. |
| 2002/0183724 A1 | 12/2002 | Neev |
| 2002/0198575 A1 | 12/2002 | Sullivan |
| 2003/0004499 A1 | 1/2003 | McDaniel |
| 2003/0004556 A1 | 1/2003 | McDaniel |
| 2003/0060811 A1 | 3/2003 | McDaniel |
| 2003/0129154 A1 | 7/2003 | McDaniel |
| 2004/0039378 A1 | 2/2004 | Lin |
| 2004/0215293 A1 | 10/2004 | Eells et al. |
| 2005/0090877 A1 | 4/2005 | Harth et al. |
| 2006/0129209 A1 | 6/2006 | McDaniel |

(56) References Cited

U.S. PATENT DOCUMENTS

| | | |
|---|---|---|
| 2006/0184214 A1 | 8/2006 | McDaniel |
| 2006/0200213 A1 | 9/2006 | McDaniel |
| 2006/0212025 A1 | 9/2006 | McDaniel |
| 2006/0265030 A1 | 11/2006 | McDaniel |
| 2007/0073276 A1 | 3/2007 | Wilkens et al. |
| 2007/0128576 A1 | 6/2007 | Boutoussov |
| 2007/0129613 A1 | 6/2007 | Rochester et al. |
| 2007/0129711 A1 | 6/2007 | Altshuler |
| 2007/0129776 A1 | 6/2007 | Robins et al. |
| 2007/0129778 A1 | 6/2007 | Dougal |
| 2007/0149900 A1 | 6/2007 | Lin |
| 2007/0149901 A1 | 6/2007 | Gordon et al. |
| 2007/0150030 A1 | 6/2007 | Pearl |
| 2007/0156208 A1 | 7/2007 | Havell |
| 2007/0167999 A1 | 7/2007 | Breden et al. |
| 2007/0168000 A1 | 7/2007 | Happawana |
| 2007/0173912 A1 | 7/2007 | Amornsiripanitch |
| 2007/0173913 A1 | 7/2007 | Anderson et al. |
| 2007/0179482 A1 | 8/2007 | Anderson |
| 2007/0179574 A1 | 8/2007 | Elliott |
| 2007/0198004 A1 | 8/2007 | Altshuler et al. |
| 2007/0208326 A1 | 9/2007 | Connors |
| 2007/0208328 A1 | 9/2007 | Boutoussov |
| 2007/0208395 A1 | 9/2007 | Leclerc |
| 2007/0208396 A1 | 9/2007 | Whatcott |
| 2007/0208400 A1 | 9/2007 | Nadkarni |
| 2007/0213696 A1 | 9/2007 | Altshuler et al. |
| 2007/0219604 A1 | 9/2007 | Yaroslavsky et al. |
| 2007/0219605 A1 | 9/2007 | Yaroslavsky et al. |
| 2007/0231255 A1 | 10/2007 | Barolet et al. |
| 2007/0239142 A1 | 10/2007 | Altshuler et al. |
| 2007/0239147 A1 | 10/2007 | Manstein et al. |
| 2007/0299486 A1 | 12/2007 | Hoenig et al. |
| 2008/0009923 A1 | 1/2008 | Paithankar |
| 2008/0015555 A1 | 1/2008 | Manstein et al. |
| 2008/0021528 A1 | 1/2008 | Carullo |
| 2008/0031833 A1 | 2/2008 | Oblong |
| 2008/0031924 A1 | 2/2008 | Gilson |
| 2008/0033516 A1 | 2/2008 | Altshuler et al. |
| 2008/0035864 A1 | 2/2008 | Fiset |
| 2008/0039906 A1 | 2/2008 | Huang et al. |
| 2008/0045933 A1 | 2/2008 | Perl |
| 2008/0051856 A1 | 2/2008 | Vizethum |
| 2008/0058783 A1 | 3/2008 | Altshuler et al. |
| 2008/0058784 A1 | 3/2008 | Manstein et al. |
| 2008/0058905 A1 | 3/2008 | Wagner |
| 2008/0065056 A1 | 3/2008 | Powell et al. |
| 2008/0065175 A1 | 3/2008 | Redmond |
| 2008/0077199 A1 | 3/2008 | Shefl |
| 2008/0082148 A1 | 4/2008 | Bernstein |
| 2008/0082149 A1 | 4/2008 | Bernstein |
| 2008/0091179 A1 | 4/2008 | Durkin et al. |
| 2008/0097278 A1 | 4/2008 | Cole |
| 2008/0097419 A1 | 4/2008 | MacFarland |
| 2008/0103560 A1 | 5/2008 | Powell et al. |
| 2008/0106896 A1 | 5/2008 | Liu et al. |
| 2008/0139901 A1 | 6/2008 | Altshuler et al. |
| 2008/0147054 A1 | 6/2008 | Altshuler et al. |
| 2008/0147148 A1 | 6/2008 | Baldacchini |
| 2008/0172112 A1 | 7/2008 | Gourgouliatos et al. |
| 2008/0172114 A1 | 7/2008 | Gourgouliatos et al. |
| 2008/0177255 A1 | 7/2008 | Bernardini |
| 2008/0183161 A1 | 7/2008 | Walneck et al. |
| 2008/0200908 A1 | 8/2008 | Domankevitz |
| 2008/0203280 A1 | 8/2008 | Rizoiu |
| 2008/0208294 A1 | 8/2008 | Pierce |
| 2008/0208295 A1 | 8/2008 | Cumbie |
| 2008/0234669 A1 | 9/2008 | Kauvar |
| 2008/0234786 A1 | 9/2008 | Cumbie |
| 2008/0255640 A1 | 10/2008 | Kipp |
| 2008/0262394 A1 | 10/2008 | Pryor |
| 2008/0262482 A1 | 10/2008 | Hantash et al. |
| 2008/0262576 A1 | 10/2008 | Creamer |
| 2008/0267814 A1 | 10/2008 | Bornstein |
| 2008/0269732 A1 | 10/2008 | Pyun |
| 2008/0269733 A1 | 10/2008 | Anderson |
| 2008/0269844 A1 | 10/2008 | Logslett |
| 2008/0269848 A1 | 10/2008 | Birmingham et al. |
| 2008/0269849 A1 | 10/2008 | Lewis |
| 2008/0275532 A1 | 11/2008 | Yamazaki |
| 2008/0281307 A1 | 11/2008 | Donahue |
| 2008/0294151 A1 | 11/2008 | Whitaker et al. |
| 2008/0294152 A1 | 11/2008 | Altshuler et al. |
| 2009/0012508 A1 | 1/2009 | Dougal |
| 2009/0018621 A1 | 1/2009 | Vogler et al. |
| 2009/0018622 A1 | 1/2009 | Asvadi et al. |
| 2009/0024116 A1 | 1/2009 | Mulhauser et al. |
| 2009/0043293 A1 | 2/2009 | Pankratov et al. |
| 2009/0062889 A1 | 3/2009 | Kiessl |
| 2009/0082836 A1 | 3/2009 | Schell |
| 2009/0088824 A1 | 4/2009 | Baird et al. |
| 2009/0105791 A1 | 4/2009 | McGinnis |
| 2009/0112192 A1 | 4/2009 | Barolet |
| 2009/0112294 A1 | 4/2009 | Huang |
| 2009/0149843 A1 | 6/2009 | Smits et al. |
| 2009/0177190 A1 | 7/2009 | Lee |
| 2009/0177253 A1 | 7/2009 | Darm et al. |
| 2009/0177256 A1 | 7/2009 | Ripper et al. |
| 2009/0187169 A1 | 7/2009 | Mirza et al. |
| 2009/0198173 A1 | 8/2009 | Samuel et al. |
| 2009/0227996 A1 | 9/2009 | Powell et al. |
| 2009/0234253 A1 | 9/2009 | Vandenbelt et al. |
| 2009/0234337 A1 | 9/2009 | Ely et al. |
| 2009/0234341 A1 | 9/2009 | Roth |
| 2009/0234342 A1 | 9/2009 | Ely et al. |
| 2009/0247932 A1 | 10/2009 | Barolet |
| 2009/0251057 A1 | 10/2009 | Son et al. |
| 2009/0254154 A1 | 10/2009 | De Taboada |
| 2009/0254156 A1 | 10/2009 | Powell et al. |
| 2009/0270845 A1 | 10/2009 | Birmingham et al. |
| 2009/0270946 A1 | 10/2009 | Spivak |
| 2009/0270953 A1 | 10/2009 | Ecker |
| 2010/0121254 A1 | 5/2010 | McDaniel |
| 2010/0256550 A1 | 10/2010 | McDaniel |

FOREIGN PATENT DOCUMENTS

| | | |
|---|---|---|
| EP | 0320080 | 6/1989 |
| EP | 1648385 | 4/2006 |
| EP | 1839705 | 3/2007 |
| EP | 1818077 | 8/2007 |
| EP | 1837050 | 9/2007 |
| EP | 1839704 | 10/2007 |
| EP | 1842571 | 10/2007 |
| EP | 1857145 | 11/2007 |
| EP | 1878466 | 1/2008 |
| EP | 1916016 | 4/2008 |
| EP | 1920798 | 5/2008 |
| EP | 1935452 | 6/2008 |
| EP | 1958662 | 8/2008 |
| EP | 1964590 | 9/2008 |
| EP | 2044901 | 4/2009 |
| EP | 2044973 | 4/2009 |
| EP | 2044974 | 4/2009 |
| EP | 2055349 | 5/2009 |
| EP | 2106198 | 9/2009 |
| EP | 2106780 | 10/2009 |
| EP | 2106824 | 10/2009 |
| EP | 2110159 | 10/2009 |
| GB | 2262043 | 6/1993 |
| GB | 2360461 | 9/2001 |
| GB | 2360641 | 9/2001 |
| JP | H01-136668 | 5/1989 |
| JP | 07-016304 | 1/1995 |
| JP | H07-100219 | 4/1995 |
| JP | H07505614 | 6/1995 |
| JP | H08308943 | 11/1996 |
| JP | H09-508031 | 8/1997 |
| JP | H10-503109 | 3/1998 |
| JP | 2000-202044 | 7/2000 |
| JP | 2002522110 | 7/2002 |
| JP | 2002535101 | 10/2002 |
| JP | 2005503388 | 2/2005 |
| JP | 2010047590 | 3/2010 |

(56) References Cited

FOREIGN PATENT DOCUMENTS

| | | |
|---|---|---|
| RU | 1724269 | 4/1992 |
| WO | 93/09847 | 5/1993 |
| WO | 93/009874 | 5/1993 |
| WO | 93/21842 | 11/1993 |
| WO | 95/19809 | 7/1995 |
| WO | 96/11723 | 4/1996 |
| WO | 96/24406 | 8/1996 |
| WO | 97/46279 | 12/1997 |
| WO | 98/11723 | 3/1998 |
| WO | 98/14453 | 4/1998 |
| WO | 98/50034 | 11/1998 |
| WO | 99/04628 | 2/1999 |
| WO | 99/19024 | 4/1999 |
| WO | 99/20336 | 4/1999 |
| WO | 99/39763 | 8/1999 |
| WO | 00/02491 | 1/2000 |
| WO | 00/02497 | 1/2000 |
| WO | 00/07514 | 2/2000 |
| WO | 00/32121 | 6/2000 |
| WO | 00/40266 | 7/2000 |
| WO | 00/44441 | 8/2000 |
| WO | 00/57804 | 10/2000 |
| WO | 00/74782 | 12/2000 |
| WO | 01/14012 | 3/2001 |
| WO | 01/40232 | 6/2001 |
| WO | 02/057811 | 7/2002 |
| WO | 03/001984 | 1/2003 |
| WO | 03/002187 | 1/2003 |
| WO | 03/005883 | 1/2003 |
| WO | 03/017824 | 3/2003 |
| WO | 03/086215 | 10/2003 |
| WO | 2004/075985 | 9/2004 |
| WO | 2004/092335 | 10/2004 |
| WO | 2005/011606 | 2/2005 |
| WO | 2005077452 | 8/2005 |
| WO | 2005/089039 | 9/2005 |
| WO | 2005/096766 | 10/2005 |
| WO | 2005/115263 | 12/2005 |
| WO | 2006/013390 | 2/2006 |
| WO | 2006/099413 | 9/2006 |
| WO | 2006/107387 | 10/2006 |
| WO | 2006/116141 | 11/2006 |
| WO | 2006/125231 | 11/2006 |
| WO | 2007/013110 | 2/2007 |
| WO | 2007/036002 | 4/2007 |
| WO | 2007/044840 | 4/2007 |
| WO | 2007/066657 | 6/2007 |
| WO | 2007/087374 | 8/2007 |
| WO | 2007/092349 | 8/2007 |
| WO | 2007/096344 | 8/2007 |
| WO | 2007/103132 | 9/2007 |
| WO | 2007/106339 | 9/2007 |
| WO | 2007/106856 | 9/2007 |
| WO | 2007/118303 | 10/2007 |
| WO | 2007/125336 | 11/2007 |
| WO | 2007/126339 | 11/2007 |
| WO | 2007/146101 | 12/2007 |
| WO | 2008/008971 | 1/2008 |
| WO | 2008/012519 | 1/2008 |
| WO | 2008/017975 | 2/2008 |
| WO | 2008/078750 | 7/2008 |
| WO | 2008/084764 | 7/2008 |
| WO | 2008/097062 | 8/2008 |
| WO | 2008/128175 | 10/2008 |
| WO | 2008/129740 | 10/2008 |
| WO | 2008/129741 | 10/2008 |
| WO | 2008/131079 | 10/2008 |
| WO | 2008/131343 | 10/2008 |
| WO | 2008/135548 | 11/2008 |
| WO | 2008/135658 | 11/2008 |
| WO | 2008/137489 | 11/2008 |
| WO | 2008/146219 | 12/2008 |
| WO | 2008/146220 | 12/2008 |
| WO | 2008/146255 | 12/2008 |
| WO | 2009/003295 | 1/2009 |
| WO | 2009/008967 | 1/2009 |
| WO | 2009/014034 | 1/2009 |
| WO | 2009/016598 | 2/2009 |
| WO | 2009/016963 | 2/2009 |
| WO | 2009/023568 | 2/2009 |
| WO | 2009/023968 | 2/2009 |
| WO | 09/038720 | 3/2009 |
| WO | 2009/056838 | 5/2009 |
| WO | 2009/059270 | 5/2009 |
| WO | 2009/064034 | 5/2009 |
| WO | 2009/089177 | 7/2009 |
| WO | 2009/107095 | 9/2009 |
| WO | 2009/117323 | 9/2009 |
| WO | 2009/118617 | 10/2009 |
| WO | 2009/121158 | 10/2009 |
| WO | 2009/123196 | 10/2009 |
| WO | 2009/125338 | 10/2009 |
| WO | 2009/132585 | 11/2009 |
| WO | 2009/137612 | 11/2009 |
| ZA | 97/007751 | 3/1998 |

OTHER PUBLICATIONS

Asawanonda et al. "308-nm Excimer Laser for the Treatment of Psoriasis," Arch Dermatol, vol. 136, May 200, pp. 619-624.*

Parrish et al. "Action Spectrum fir Phototherapy of Psoriasis," J0umal of Investigative Dermatology, vol. 76, No. 5, 1981, pp. 359-362.*

US Office Action dated Jun. 13, 2011 issued in U.S. Appl. No. 11/346,622, filed Feb. 3, 2006.

US Rce and Response filed Aug. 18, 2011 to US Office Action dated Jun. 13, 2011 issued in U.S. Appl. No. 11/346,622, filed Feb. 3, 2006.

US Office Action dated Sep. 30, 2010 issued in U.S. Appl. No. 11/346,622, filed Feb. 3, 2006.

US Response filed Mar. 30, 2011 to US Office Action dated Sep. 30, 2010 issued in U.S. Appl. No. 11/346,622, filed Feb. 3, 2006.

US Office Action dated Apr. 11, 2012 issued in U.S. Appl. No. 12/583,578, filed Aug. 21, 2009.

US RCE and Response filed Oct. 11, 2012 to US Office Action dated Apr. 11, 2012 issued in U.S. Appl. No. 12/583,578, filed Aug. 21, 2009.

US Office Action dated Jul. 21, 2011 issued in U.S. Appl. No. 12/583,578, filed Aug. 21, 2009.

US Response filed Sep. 21, 2011 to US Office Action dated Jul. 21, 2011 issued in U.S. Appl. No. 12/583,578, filed Aug. 21, 2009.

US Office Action dated May 10, 2011 issued in U.S. Appl. No. 12/550,749, filed Aug. 31, 2009.

US Response filed Sep. 26, 2011 to US Office Action dated May 10, 2011 issued in U.S. Appl. No. 12/550,749, filed Aug. 31, 2009.

US Office Action dated Jan. 18, 2012 issued in U.S. Appl. No. 12/550,749, filed Aug. 31, 2009.

US RCE and Response filed Jul. 17, 2012 to US Office Action dated Jan. 18, 2012 issued in U.S. Appl. No. 12/550,749, filed Aug. 31, 2009.

US Notice to Applicant Regarding Non-Compliant Amendment dated Oct. 5, 2011 issued in U.S. Appl. No. 12/550,749, filed Aug. 31, 2009.

US Response filed Jul. 17, 2011 to US Notice to Applicant Regarding Non-Compliant Amendment dated Oct. 5, 2011 issued in U.S. Appl. No. 12/550,749, filed Aug. 31, 2009.

US Office Action dated May 11, 2011 issued in U.S. Appl. No. 12/550,799, filed Aug. 31, 2009.

US Terminal Disclaimer and Response filed Sep. 26, 2011 to US Office Action dated May 11, 2011 issued in U.S. Appl. No. 12/550,799, filed Aug. 31, 2009.

US Terminal Disclaimer Decision issued Nov. 15, 2011 in U.S. Appl. No. 12/550,799, filed Aug. 31, 2009.

US Notice to Applicant Non-Compliant Amendment dated Feb. 16, 2012 in U.S. Appl. No. 12/550,799, filed Aug. 31, 2009.

US Response filed Nov. 15, 2011 to Notice to Non-Compliant Amendment dated Feb. 16, 2012 in U.S. Appl. No. 12/550,799, filed Aug. 31, 2009.

US Office Action dated Dec. 3, 2012 in U.S. Appl. No. 12/550,799, filed Aug. 31, 2009 (Response not filed yet.).

Response to Final Office Action dated Jan. 5, 2009 for U.S. Appl. No. 11/116,434.

(56) References Cited

OTHER PUBLICATIONS

Final Office Action dated Jan. 5, 2009 for U.S. Appl. No. 11/116,434.
Amendment to Non-Final Rejection dated Feb. 20, 2008 for U.S. Appl. No. 11/116,434.
Non-Final Rejection dated Feb. 20, 2008 for U.S. Appl. No. 11/116,434.
Amendment to Final Office Action dated Jun. 29, 2007 for U.S. Appl. No. 11/116,434.
Final Rejection dated Jun. 29, 2007 for U.S. Appl. No. 11/116,434.
Amendment to Non-Final Rejection dated Jan. 9, 2007 for U.S. Appl. No. 11/116,434.
Non-Final Rejection dated Jan. 9, 2007 for U.S. Appl. No. 11/116,434.
Amendment to Non-Final Rejection filed Sep. 26, 2005 for U.S. Appl. No. 09/876,157.
Miscellaneous Action regarding Drawing Inconsistency dated Aug. 24, 2005 for U.S. Appl. No. 09/876,157.
Amendment to Non-Final Rejection dated Apr. 8, 2004 U.S. Appl. No. 09/876,157.
Non-Final Rejection dated Apr. 8, 2004 for U.S. Appl. No. 09/876,157.
Response to Restriction Requirement dated Jul. 22, 2003 for U.S. Appl. No. 09/876,157.
Requirement for Restriction/Election dated Jul. 22, 2003 for U.S. Appl. No. 09/876,157.
Preliminary Amendment filed Jan. 7, 2002 for U.S. Appl. No. 09/876,157.
Amendment to Final Office Action dated Jan. 25, 2008 for U.S. Appl. No. 11/783,538.
Final Rejection dated Jan. 25, 2008 for U.S. Appl. No. 11/783,538.
Amendment to Non-Final Rejection dated Aug. 22, 2007 for U.S. Appl. No. 11/783,538.
Non-Final Rejection dated Aug. 22, 2007 for U.S. Appl. No. 11/783,538.
Non-Final Rejection dated Dec. 30, 2005 for U.S. Appl. No. 09/819,082.
Preliminary Amendment filed Feb. 15, 2001 for U.S. Appl. No. 09/819,082.
Amendment After Notice of Allowance filed Aug. 1, 2008 for U.S. Appl. No. 09/819,083.
Amendment to Final Office Action filed Apr. 17, 2008 for U.S. Appl. No. 09/819,083.
Final Rejection dated Jan. 24, 2008 for U.S. Appl. No. 09/819,083.
Amendment to Non-Final Rejection dated May 15, 2007 for U.S. Appl. No. 09/819,083.
Non-Final Rejection dated May 15, 2007 for U.S. Appl. No. 09/819,083.
Amendment to Final Office Action dated Dec. 22, 2006 for U.S. Appl. No. 09/819,083.
Final Rejection dated Dec. 22, 2006 for U.S. Appl. No. 09/819,083.
Amendment to Non-Final Rejection dated Mar. 24, 2006 for U.S. Appl. No. 09/819,083.
Non-Final Rejection dated Mar. 24, 2006 for U.S. Appl. No. 09/819,083.
Advisory Action dated Dec. 1, 2005 for U.S. Appl. No. 09/819,083.
Amendment to Final Office Action dated Sep. 1, 2005 for U.S. Appl. No. 09/819,083.
Final Rejection dated Sep. 1, 2005 for U.S. Appl. No. 09/819,083.
Amendment to Non-Final Rejection dated Dec. 15, 2004 for U.S. Appl. No. 09/819,083.
Non-Final Rejection dated Dec. 15, 2004 for U.S. Appl. No. 09/819,083.
Amendment to Non-Final Rejection dated Jan. 14, 2004 for U.S. Appl. No. 09/819,083.
Non-Final Rejection dated Jan. 14, 2004 for U.S. Appl. No. 09/819,083.
Preliminary Amendment filed Feb. 15, 2001 for U.S. Appl. No. 09/819,083.
Non-Final Rejection dated Feb. 19, 2003 for U.S. Appl. No. 09/819,083.
Amendment to Non-Final Rejection dated Feb. 19, 2003 for U.S. Appl. No. 09/819,083.
Preliminary Amendment filed May 2, 2005 for U.S. Appl. No. 11/119,378.
Non-Final Rejection dated Jun. 5, 2006 for U.S. Appl. No. 11/119,378.
Amendment to Non-Final Rejection dated Jun. 5, 2006 for U.S. Appl. No. 11/119,378.
Preliminary Amendment filed Aug. 29, 2005 for U.S. Appl. No. 11/212,916.
Non-Final Rejection dated Sep. 25, 2007 for U.S. Appl. No. 11/212,916.
Amendment to Non-Final Rejection dated Sep. 25, 2007 for U.S. Appl. No. 11/212,916.
Final Rejection dated Mar. 25, 2008 for U.S. Appl. No. 11/212,916.
Non-Final Rejection dated Jun. 19, 2008 for U.S. Appl. No. 11/332,517.
Non-Final Rejection dated Dec. 19, 2002 for U.S. Appl. No. 09/986,367.
Amendment to Non-Final Rejection dated Dec. 19, 2002 for U.S. Appl. No. 09/986,367.
Final Rejection dated Aug. 12, 2003 for U.S. Appl. No. 09/986,367.
Amendment to Final Office Action dated Aug. 12, 2003 for U.S. Appl. No. 09/986,367.
Advisory Action dated Mar. 8, 2004 for U.S. Appl. No. 09/986,367.
Non-Final Rejection dated Sep. 22, 2004 for U.S. Appl. No. 09/986,367.
Amendment to Non-Final Rejection dated Sep. 22, 2004 for U.S. Appl. No. 09/986,367.
Non-Final Rejection dated Jun. 26, 2008 for U.S. Appl. No. 11/366,811.
Non-Final Rejection dated Jun. 25, 2008 for U.S. Appl. No. 11/346,622.
Amendment to Non-Final Rejection dated Jun. 25, 2008 for U.S. Appl. No. 11/346,622.
Final Office Action dated Jan. 6, 2010 for U.S. Appl. No. 11/346,622.
Response to Final Office Action dated Jan. 6, 2010 for U.S. Appl. No. 11/346,622.
Advisory Action dated Mar. 12, 2010 for U.S. Appl. No. 11/346,622.
Jarrousse, F., et al. (2001). "Identification of clustered cells in human hair follicle responsible for MMP-9 gelatinolytic activity: Consequences for the regulation of hair growth." International Journal of Dermatology, 40(6), pp. 385-392.
Langbein, et al. (2001). "Figure 8." Journal of Biological Chemistry, 276(37), pp. 35123.
King, A., et al. (2004). "Mitochondria-derived reactive oxygen species mediate blue light-induced death of retinal pigment epithelial cells." Photochemistry and Photobiology, 79(5), pp. 470-475.
"The EpiOcular™ Model." http://www.mattek.com/pages/products/epiocular. Mattek Corporation. Accessed: Apr. 27, 2005.
"Folliquant®: A range of in vivo assays of hair follicle damage and alopecia." EpiStem® Ltd. Copyright 2003 Epistem Ltd.
Davis, S.C., et al. (2004). "To examine the effect of GentleWaves LED photomodulation device on deep partial thickness wound healin." Preliminary Protocol: Deep Partial thickness wound study. Department of Dermatology and Cutaneous Surgery, University of Miami School of Medicine.
"Virulite CC® . . . The ORIGINAL Cold Sore Machine." http://www.virulite.com/technical_information.html Date accessed: Jan. 26, 2008.
Christensen, B. (2008). "Forced resonance ultra-short pulse laser kills viruses dead." Technovelogy.com Where Science Meets Fiction, http://www.technovelogy.com/ct/Science-Fiction-News.asp?NewsNum=1311. Date Accessed: Jan. 26, 2008.
"Visual Signal Transduction." Biocarta http://www.biocarta.com/pathfiles/h_rhodospinPathway.asp Date Accessed: Aug. 29, 2005.
Epstein, P. (2007). "Trials that matter: Two faces of progress in the treatment of age-related macular degeneration." Annals of Internal Medicine, 146(7), pp. 532-534.
Ostler, E.L. et al. (2000) "Telomerase and the cellular lifespan: Implications of the aging process." Journal of Pediatric Endocrinology and Metabolism, 13(6), pp. 1467-1476.

(56) References Cited

OTHER PUBLICATIONS

Lou, H. J. et al.(2002). "Lighting the way: Molecular beacons offer a highly sensitive, flexible method for DNA analysis." SPIE's OEMagazine, Feb., pp. 23-25.
"The Relief Light: A sensible alternative to 'soft' laser technology." Retrieved: http://www.fredomunlimited.net/relief%20light.htm Date Accessed: Feb. 9, 2002.
Stern, R. et al. (2001)."Hyaluronidase can modulate expression of CD44." Experimental Cell Research, 265, pp. 1-10.
Mio, K. et al. (2000). "Evidence that the serum inhibitor of hyaluronidase may be a member of the inter-a-inhibitor family." Journal of Biological Chemistry, 275(42), pp. 32413-32421.
Mortimer, A.J., & Dyson, M. (1988). "The effect of therapeutic ultrasound on calcium uptake in fibroblasts." Ultrasound in Medicine and Biology, 14(6), pp. 499-506.
Illel, Brigette, et al. (1991), "Follicles Play an Important Role in Percutaneous Absorption," Journal of Pharmaceutical Sciences 80(5).
Finlay, A., et al., "A Fluorescence Photographic Photomeric Technique to assess Stratum Corneum Turnover Rate and Barrier Function in Vivo", British Journal of Dermatology, 1982, 107, 35-42.
Burgess, "Researchers Identify Key to Phototropism", Biophotonics International, Nov./Dec. 1999, pp. 22-23.
Green, C., et al. (1988), "311 nm UVB Phototherapy: an Effective Treatment for Psoriasis", Br J Dermatol. 119, pp. 694-696.
Callaghan et al. (1996), "Reactive Oxygen Species Inducible by Low-intensity Laser Irradiation Alter DNA Synthesis in the Hemopoietic Cell Line", U937, Lasers Surg. Med. 19(2):201-206.
Castro (Sep. 1983), "Effects of the Nd:YAG Laser on DNA Synthesis and Collagen Production in Human Skin Fibroblast Cultures", Annals of Plastic Surgery 11, pp. 3.
Ceccherelli et al. (1989), "Diode Laser in Cervical Myofascial Pain: A Double-blind Study Versus Placebo," The Clinical Journal of Pain 5:301-304.
Chung et al. (1996), "Histological Responses of Port Wine Stains in Brown Skin After 578 nm Copper Vapor Laser Treatment", Lasers Surg. Med. 18(4):358-366.
Roden, Dan, MD, "Electrophysiology, Pacing and Arrhythmia", Clin. Cardiol, 20, 285-290 (1997).
Bruer, Miklos M., "Ultrasonic Radiation for Hair Treatments", Cosmetics & Toiletries, vol. 113, pp. 67-75, Jun. 1998.
Webster, D. F., et al., "The Role of Cavitation in the In Vitro Stimulation of Protein Synthesis in Human Fibroblasts by Ultrasound," Ultrasound in Med & Biol., 4, pp. 343-351.
Webster, D. F, et al., "The Role of Ultrasound-Induced Cavitation in the 'In Vitro' Stimulation of Collagen Synthesis in Human Fibroblasts," Ultrasonics, pp. 33-37 (1980).
Castro, D. J., et al. (Dec. 1987), "Biostimulative Effects of Nd: YAG Q-Switch Dye on Normal Human Fibroblast Cultures: Study of a New Chemosensitizing Agent for the Nd: YAG Laser", Laryngoscope, 97(12), pp. 1454-1459.
Database WPI Week 200046 Derwent Publications Ltd., London, GB; AN 2000-511628; XP002373743 & JP 2000 202044 A (Yamana Co Ltd.) Jul. 25, 2000 *abstract*.
Draper, David, et al. (1995), "Temperature Changes in Deep Muscles of Humans During Ice and Ultrasound Therapies: an in Vivo Study", JOSPT 12(3).
Karu et al. (1996), "Effects of Monochromatic Low-intensity Light and Laser Irradiation on Adhesion of the HeLa Cells in Vitro", Lasers Surg. Med. 18(2):171-177.
Tachibana, Katsuro (1992), "Transdermal Delivery of Insulin to Allosxan-Diabetic Rabbits by Ultrasound Exposure", Pharmaceutical Research 9(7).
Edwards, (May 2001) "Keeping Up with the LEDs," Photonics Spectra.
Gann, Nancy, "Ultrasound: Current Concepts", Electrotherapy, vol. 11, No. 4, Jul./Aug. 1991.
Tur, Ethel, et al. (1991), "Percutaneous Penetration of Methy Nicotinate at Three Anatomic Sites: Evidence for an Appendagael Contribution to Transport?", Skin Pharmacol 4, pp. 230-234.

Heuber, F., et al. (1994), "Percutaneous Absorption of Estradiol and Progesterone in Normal and Appendage-Free Skin of the Hairless Rat: Lack of Importance of Nutritional Blood Flow", Skin Pharmacol 7, pp. 245-256.
Freeman et al. (2004), "NGF Deprivation-induced Gene Expression: After Ten Years, Where Do We Stand?," Chapter 8 in Progress in Brain Research 146, Elsevier B.V., 111-126.
Reddy, G. Kesave, et al. (1998), "Laser Photostimulation of Collagen Production in Healing Rabbit Achilles Tendons", Lasers in Surgery and Medicine, 22, pp. 281-287.
Nicolau, G., et al. (1987), "Deposition of Viprostol (a Synthetic PGE2 Vasodilator) in the Skin Following Topical Administration to Laboratory Animals", Xenobiotica 17(9), pp. 1113-1120.
Gao et al. (Jul. 13, 2004), "Induction of Phase 2 Genes by Sulforaphane Protects Retinal Pigment Epithelial Cells Against Photooxidative Damage", PNAS 101(28:10446-10451).
Giamundo (May 2001), "A Little Enlightenment," Photonics Spectra.
Menon, Gopinathan K., et al. (1994), "High-Frequency Sonophoresis: Permeation Pathways and Structural Basis for Enhanced Permeability", Skin Pharmacol. 7, pp. 130-139.
Gupta et al. (1998), "The Use of Low Energy Photon Therapy (LEPT) in Venous Leg Ulcers: A Double-Blind, Placebo-Controlled Study", Dermatol. Surg. 24, pp. 1383-1386.
Gupta, A. K, et al. (1997) "The Use of Low Energy Photon Therapy in the Treatment of Leg Ulcers—A Preliminary Study," Journal of Dermatological Treatment 8(2), pp. 103-108.
Van Weelden, H., et al. (1990), "Comparison of Narrow band UV-B Phototherapy and PUVA Photochemotherapy in the Treatment of Psoriasis", Acta Dermatol Venereol (Stockh) 70, pp. 212-215.
Schaefer, Hans, et al. (1996), "Skin Barrier Principles of Percutaneous Absorption", pp. 153 and 175.
Benson, Heather A., et al, (1991), "Influence of Ultrasound on the Percutaneous Absorption of Nicotinate Esters," Pharmaceutical Research 8(2), pp. 204-209.
Benson, Heather A., et al. (1988), "Transmission of Ultrasound Energy Through Topical Pharmaceutical Products", Physiotherapy 74(11), pp. 587-589.
Huang et al. (Aug. 2004), "Downregulation of ATP Synthase Subunit-6, Cytochrome c Oxidase-III, and Nadh Dehydrogenase-3 by Bright Cyclic Light in the Rat Retina". Investigative Ophthalmology & Visual Science 45 (8):2489-2496.
Omura, T., "Hemoprotein H-450 Identified as a Form of Cytocherome P-450 Having an Endorgenous Ligand at the 6th Coordination Position of the Heme (Abstract)", J. Biochem (Tokyo), Nov. 1984; 96(5)1491-1500.
Kao, Jr., et al. (1988), "In Vitro Percutaneous Absorption in Mouse Skin: Influence of Skin Appendages", Toxicology and Applied Pharmacology 94, pp. 93-103.
Ferry, James, et al. (1990), "Relationship Between Contact Time of Applied Dose and Percutaneous Absorption of Minoxidil from a Topical Solution". Journal of Pharmaceutical Sciences 79(6), pp. 483-486.
Kumar, Saran, et al. (1992), "Studies of in Vitro Skin Permeation and Retention of a Leukotriene Antagonist from Topical Vehicles with a Hairless Guinea Pig Model", Journal of Pharmaceutical Sciences, vol. 81, No. 7.
Mitragotri, Samir, et al. (Jun. 1995), "A Mechanistic Study of Ultrasonically-Enhanced Transdermal Drug Delivery," Journal of Pharmaceutical Sciences, vol. 84, No. 6.
Egbaria, Kamel, et al. (1992), "Absorption of Fluorescein Dyes on Albumin Microspheres", Pharmaceutical Research 9, pp. 629-635.
Ortonne, Jean-Paul, "Psoralen Therapy in vitiligo", Clinics in Dermatology, 1989; vol. 7, No. 2, April-June.
Tsai, Jui-Chen, et al. (1992), "Drug and Vehicle Deposition from Topical Applications: Use of Vitro Mass Balance Technique with Minoxidil Solutions", Journal of Pharmaceutical Sciences, vol. 81, No. 8.
Chen, Huxiong, et al. (1995), "Chemical Generation of Acoustic Waves: A Giant Photoacoustic Effect", Science 270.
Office Action dated Oct. 2, 2009 for Canadian Patent Application No. 2457590.
Response to Office Action dated Oct. 2, 2009 for Canadian Patent Application No. 2457590.

(56) References Cited

OTHER PUBLICATIONS

Office Action dated Dec. 30, 2010 in Canadian Patent Application No. 2,457,590.
Office Action dated May 6, 2010 in Canadian Patent Application No. 2,457,590.
Response to Office Action dated May 6, 2010 in Canadian Patent Application 2,457,590.
Office Action dated Aug. 25, 2006 for European Patent Application No. 02761449.4-1216.
Response to Office Action dated Aug. 25, 2006 for European Patent Application No. 02761449.4-1216.
Office Action dated Jul. 31, 2007 for European Patent Application No. 02761449.4-1216.
Response to Office Action dated Jul. 31, 2007 for European Patent Application No. 02761449.4-1216.
Result of Consultation by Telephone with Applicant/Representative dated Aug. 28, 2008 for European Patent Application No. 02761449.4-1216.
Decision to Refuse a European Application dated Mar. 31, 2009 for European Patent Application No. 02761449.4-1216.
Office Action dated May 13, 2008 for Israeli Patent Application No. 160505.
Examination Report dated Apr. 28, 2005 for New Zealand Patent Application No. 531491.
Written Opinion dated Feb. 5, 2004 for PCT Patent Application No. PCT/US02/26627.
First Statement of Proposed Amendments dated Dec. 21, 2005 for Australian Patent Application No. 2002357695.
Official Report dated Jun. 28, 2007 for Australian Patent Application No. 2002357695.
Response to Official Report dated Jun. 28, 2007 for Australian Patent Application No. 2002357695.
Official Report dated Dec. 19, 2007 for Australian Patent Application No. 2002357695.
Office Action dated Aug. 9, 2006 for Canadian Patent Application No. 2465906.
Response to Office Action dated Aug. 9, 2006 for Canadian Patent Application No. 2465906.
Office Action dated Mar. 27, 2007 for Canadian Patent Application No. 2465906.
Response and Amendment to Office Action dated Mar. 27, 2007 for Canadian Patent Application No. 2465906.
Office Action dated Nov. 23, 2007 for Canadian Patent Application No. 2465906.
Response to Office Action dated May 13, 2008 for Israeli Patent Application No. 160505.
Office Action dated Mar. 1, 2007 for Indian Patent Application No. 00332/KOLNP/2004.
Response to Office Action dated Mar. 1, 2007 for Indian Patent Application No. 00332/KOLNP/2004.
Office Action dated Nov. 10, 2008 for Korean Patent Application No. 700267712004.
Office Action dated Feb. 22, 2012 for Japanese Patent Application No. 2009-236857.
Office Action dated Sep. 12, 2012 for Japanese Patent Application No. 2009-236857.
Response to Office Action dated Sep. 12, 2012 for Japanese Patent Application No. 2009-236857.
Official Letter dated Sep. 3, 2007 for Mexican Patent Application No. 2004/001710.
2nd Official Action dated Sep. 19, 2008 for Mexican Patent Application No. 2004/001710.
3rd Official Action dated Dec. 8, 2010 for Mexican Patent Application No. 2004/001710.
Response to 3rd Official Action dated Dec. 8, 2010 for Mexican Patent Application No. 2004/001710.
Response to Office Action dated Nov. 23, 2007 for Canadian Patent Application 2465906.
Office Action dated Oct. 5, 2010 for Canadian Patent Application No. 2465906.
Response to Office Action dated Oct. 5, 2010 for Canadian Patent Application No. 2465906.
Office Action dated Jun. 30, 2011 for Canadian Patent Application No. 2465906.
Response to Office Action dated Jun. 30, 2011 for Canadian Patent Application No. 2465906.
Office Action dated Mar. 3, 2010 Canadian Patent Application 2465906.
Response to Office Action dated Mar. 3, 2010 for Canadian Patent Application No. 2465906.
Office Action dated Oct. 14, 2005 for Chinese Patent Application No. 028247698.
Response to Office Action dated Oct. 14, 2005 for Chinese Patent Application No. 028247698.
Second Office Action dated Apr. 11, 2008 for Chinese Patent Application No. 028247698.
Response to Second Office Action dated Apr. 11, 2008 for Chinese Patent Application No. 028247698.
Third Office Action dated Aug. 15, 2008 for Chinese Patent Application No. 028247698.
Office Action dated Sep. 11, 2006 for European Patent Application No. 02792232.7.
Response to Office Action dated Sep. 11, 2006 for European Patent Application No. 02792232.7.
Office Action dated Jul. 2, 2007 for European Patent Application No. 02792232.7.
Newman, J.T., Nellrmoe, M.D., & Carnett, J.L. (1992). "Hydrocortisone phonophoresis: A literature review," Journal of the American Podiatric Medical Association, 82(8), pp. 432-435.
Menon, G.K., Bommannan, D.B., & Elias, P.M. (1993), "High-frequency sonophoresis: Permeation pathways and structural basis for enhanced permeability," Skin Pharmacol, 7. pp. 130-139.
Mitragotri, S., Blankschtein, D., & Lander, R. (1995). "Ultrasound-mediated transdermal protein delivery," Science, 269. pp. 850-853.
Draper, D.O., Castel, J.C., & Castel, D. (1995). "Rate of temperature increase in human muscle during 1 MHz and 3 MHz continuous ultrasound," JOSPT, 22(4). pp. 142-150.
Rougier, A., et al. (1983). "In vivo correlation between stratum corneum reservoir function ad percutaneous absorption," The Journal of Investigative Dermatology, 81. pp. 275-278.
Zabel, K. (1999). "Wrinkle removal without the wound," Dermatology Times, 20(6).
Zabel, K. (1999). "Future of laser surgery: Unexplored benefits await," Dermatology Times, 20(6).
Gniadecka, M., et al. (1994). "Ultrasound structure and digital image analysis of the subepidermal low echogenic band in aged human skin: Diurnal changes and interindividual variability," The Journal for Investigative Dermatology, 102(3). pp. 362-365.
Mitragotri, S., et al. (1995). "A mechanistic study of ultrasonically-enhanced transdermal drug delivery," Journal of Pharmaceutical Science, 84(6), pp. 697-706.
Meidan, V.M., et al. (1998). "Low Intensity ultrasound as a probe to elucidate the relative follicular contribution to total transdermal absorption," Pharmaceutical Research, 15(1). pp. 85-92.
Mitragotri, S., Blankschtein, D., & Langer, R. (1996). "Transdermal drug delivery using low-frequency sonophoresis," Pharmaceutical Research, 13(3). pp. 411-420.
Mitragotri, S., Blankschtein, D., & Langer, R. (1986). "An explanation for the variation of the sonophoretic transdermal transport enhancement from drug to drug," Journal of Pharmaceutical Science, 86(10). pp. 1190-1192.
Hippius, M., et al. (1998). "In vitro investigations of drug release and penetration-enhancing effect of ultrasound on transmembrane transport of flufenamic acid," International Journal of Clinical Pharmacological,Therapy, and Toxicology, 36(2). pp. 107-111.
Miyazaki, S., et al. (1992). "External control of drug release and penetration. Vi. enhancing effect of ultrasound on the transdermal absorption of indomethacin from an ointment in rats," Chemical and Pharmaceutical Bulletin, 40(10). pp. 2826-2830.
Asano, J., et al. (1997). "Effect of pulsed output ultrasound on the transdermal absorption of indomethacin from an ointment in rats," Biological and Pharmaceutical Bulletin, 20(3). pp. 288-291.

(56) References Cited

OTHER PUBLICATIONS

Miyazaki, S., et al. (1991). "External control of drug release and penetration: Enhancement of the transdermal absorption of indomethacin by ultrasound irradiation," Journal of Pharmaceutical Pharmacology, 43(2). pp. 115-116.

Bommannan, D., et al. (1992). "Sonophoresis.l. The use of high-frequency ultrasound to enhance transdermal drug delivery," Pharmaceutical Research, 9(4). pp. 559-564.

Tachibana, K., Tachibana, S. (1998). "Application of ultrasound energy as a new drug delivery system," Nippon Rinsho, 56(3). pp. 584-588.

Byl, N.N. (1995). "The use of ultrasound as an enhancer for transcutaneous drug delivery: phonophoresis," Physical Therapy, 75(6). pp. 539-553.

Hikima, T.. Hirai, Y,, & Tajo. K. (1998). "Effect of ultrasound application on skin metabolism of prednisolone 21-acetate," Pharmaceutical Research. 15(11). pp. 1680-1683.

Yata, N. (1998). "Enhancement of drug absorption by iontophoresis and phonophoresis and clinical application," 21 Nippon Rinsho, 56(3). pp. 608-612.

Kimura, I.F., et al, (1998). "Effects of two ultrasound devices and angles of application on the temperature of tissue phantom." Journal of Orthopedic and Sports Physical Therapy, 27(1), pp. 27-31.

Mikulak, S.A., Vangsness, C.T., & Nimmi, M.E. (1998). "Transdermal del very and accumulation of indomethacin in subcutaneous tissues in rats," Journal of Pharmaceutical Pharmacology, 50(2). pp. 153-158.

Murakami, T., et al. (1998). "Topical delivery of keloid therapeurtic drug, trailast, by combined use of oleic acid and 24 propylene glycol as a penetration enhancer: Evaluation by skin microdialysis in rats," Journal of Pharmaceutical Pharmacology, 50(1). pp. 49-54.

Stott, P.W., Williams, A.C., & Barry, B.W. (1998). "Transdermal delieevery from eutictic systems: Enhanced permeation 25 of a model drug, ibuprofen." Journal of Controlled Release, 50(1-3). pp. 297-308.

Morimoto,Y., & Fujimoto, S. (1985). "Albumin microspheres as drug carriers," Critical Review of Therapeutic Drug 26 Carrier Systems, 2(1). pp. 19-63.

Johnson, M.E., et al. (1996). "Synergistic effects of chemical enhancers and therapeutic ultrasound on transdermal 27 drug delivery," Journal of Pharmaceutical Science, 85(7). pp. 670-679.

Illel, B. (1997). "Formulation for transfollicular drug administration: some recent advances," Critical Review of 28 Therapeutic Drug Carrier Systems, 14(3). pp. 207-219.

Mitragotri, S. (2000). "Synergistic effect of enhancers for transdermal drug delivery," Pharmaceutical Research, 17(11). 29 pp. 1354-1359.

Frenkel, V., Kimmel, E., & Iger, Y. (2000). "Ultrasound-facilitated transport o ver chloride (AgCI) particles in fish skin," Journal of Controlled Release, 68(2), pp. 251-161.

Mitragotri, S. (2001). "Effect of therapeutic ultrasound on partition and diffusion coefficients in human stratum corneum." Journal of Controlled Release, 71( 1). pp. 23-29.

Tan, H.S., Pfister, W.R. (1999). "Pressure-sensitve adhesives for transdermal drug delivery systems," PSTT, 2(2). pp. 60-69.

Tajima, S., & Pinnel. S.R. (1996). "Ascorbic acid preferentially enhances type I and III collagen gene transcription in human skin fibroblasts," Journal of Dermatological Science, 11(3). pp. 250-253.

Castro, D.J., et al. (1987). "Biostimulative effects of Nd: YAG Q-switch dye on normal human fibroblast cultures: Study of a new chemosensitizing agent for the Nd:YAG laser," Laryngoscope, 97(12). pp. 1454-1459.

Omura, T., et al. (1984). "Hemoprotein H-450 identified as a form of cytochrome P-450 having an endogenous ligand at the 6th coordination position of the heme," Journal of Biochemistry, 96(5). pp. 1491-1500.

Hrnjak, M., et al. (1995). "Stimulatory effect of low-power density He-Ne laser radiation on human fibroblasts n. vitro," Vojnosanit Pregl, 52(6). pp. 539-546.

Krammer, B., Hubmer, A., & Hermann, A. (1993). "Photodynamic effects on the nuclear envelope of human skin fibroblasts," Journal of Photochemistry and Photobiology, 17(2). pp. 109-114.

Lyons, R.F., et al. (1987). "Biostimulation of wound healing in vivo by a helium-neon laser," Annals of Plastic Surgery, 18(1). pp. 47-50.

Yu, W., Naim, J.O., & Lanzafame, R.J. (1997). "Effects of photostimulation on wound healing in diabetic mice," Lasers in Surgery and Medicine, 20(1). pp. 56-63.

Morrone, G., et al. (1998). "In vitro experimental research of rabbit condrocytes biostimulation with diode laser Ga-Al-As: a preliminary study," Artificial Cells, Blood Substitutes, and Biotechnology, 26(4). pp. 437-439.

Van Breugel, H.H., & Bar, P.R. (1992). "Power density and exposure time of He-Ne laser irradiation are more important than total energy dose in photo-biomodulation of human fibroblasts in vitro," Lasers in Surgery and Medicine, 12(5). pp. 528-537.

"Apoptosis," dated Sep. 19, 2005, located at http:www.neuro.wustl. edu/NEUROMUSCULAR/mother/apoptosis.htm> retrieved on Oct. 24, 2007 (5 pages).

"Chlorophyll," from Wikipedia located at http://de.wikipedia.org/wiki/Chlorophyll, visited on Jul. 18, 2007 (4 pages).

"Phorphin," from Wikipedia located at <en.wikipedia.org/wiki/Porphine, visited on Jul. 18, 2007 (2 pages).

Doukas, A. et al. (1996) "Physical Characteristics and Biological Effects of Laser-Induced Stress Waves", Ultrasound in Med. & Biol. 22(2), pp. 151-164.

Abergel et al., (Feb. 1987) "Biostimulation of Wound Healing by Lasers: Experimental Approaches in Animal Models and in Fibroblast Cultures", J. Dermatol. Surg. Oncol. 13/(2) pp. 127-133.

Drastichova, V. et al., (1973), "Strengthening of Sutured Skin Wound with Ultrasound in Experiments on Animals", Acta Chirurgiae Plasticae 15, pp. 114-119.

Purkyne, J.E., "Ultrasound Effect on Collagen Synthesis and Deposition in Differently Localized Experimental Granulomas", Acta Chirurgiae Plasticae (19, 3-4, 1977) (marked up).

Guffey, Stephen et al., "More Than a Thermal Modality: Ultrasound", Advance Rehabilitation, Jul./Aug. 1994.

Rolland, Alain et al. (1993) "Site-Specific Drug Delivery to Pilosebaceous Structures Using Polymeric Microspheres", Pharmaceutical Research 10(12), pp. 1738-1744.

Enwemeka, Chukuka S., "The Effects of Therapeutic Ultrasound on Tendon Healing", Am. J. Phys. Med. Rehabil., vol. 68 No. 6, pp. 283-287, Dec. 1989.

Tachibana, Katsuro et al., "Use of Ultrasound to Enhance the Local Anesthetic Effect of Topically Applied Aqueous Lidocaine", Anesthesiology, V. 78 No. 6, Jun. 1993.

Lyons, R.F. et al., "Biostimulation of Wound Healing in Vivo by a Helium-Neon Laser", Ann Plast Surg, Jan. 1987; 18(1):47-50.

Wester, Ronald et al., "Variations in Percutaneous Absorption of Testosterone in Rhesus Monkey Due to Anatomic Site of Application and Frequency of Application", Arch Dermatol Res., 267, 229-235 (1980).

Franz, Thomas, "Percutaneous Absorption of Minoxidil in Man", Arch Dermatol, vol. 121, Feb. 1985.

Menon, Gopinathan K. et al., "Ultrasound Localization of Calcium in Psoriatic and Normal Human Epidermis", Arch Dermatol, vol. 127, Jan. 1991.

Byl, Nancy N. et al., "Low Dose Ultrasound Effects of Wound Healing: A Controlled Study with Yucatan Pigs", Arch Phys Med Rehabil., vol. 73, Jul. 1992 (marked up).

Phillips, Charlotte, et al., "Ascorbic Acid and Transforming Growth Factor-B1 Increase Collagen Biosynthesis via Different Mechanisms: Coordinate Regulation of Proal(1) and Proal(III) Collagens", Archives of Biochemistry and Biophysics, vol. 295, No. 2, 1992, pp. 397-403.

Darr, Douglas, et al., "Ascorbic Acid and Collagen Synthesis: Rethinking a Role for Lipid Peroxidation", Archives of Biochemistry and Biophysics, vol. 307, No. 2, 1993, pp. 331-335.

Menezes, Salatiel, et al., (1998) "Non-Coherent Near Infrared Radiation Protects Normal Human Dermal Fibroblasts from Solar Ultraviolet Toxicity".

(56) References Cited

OTHER PUBLICATIONS

Morrone, G., et al., "In Vitro Experimental Research of Rabbit Condrocytes Biostimulation with Diode Laser Ga-Al-As: a Preliminary Study", Artif Cells Blood Substit Immobil Biotechnol. Jul., 1998; 26(4):437-439 (Abstract).
Asawanonda et al., "308-nm Excimer Laser for the Treatment of Psoriasis", Arch Dermatol, vol. 136, May 2000, pp. 619-624.
Krammer, B. et al. (Feb. 1993) "Photodynamic Effects on the Nuclear Envelope of Human Skin Fibroblasts", Journal of Photochem Photobiol. B: Biol. 17(2), pp. 109-114.
Bommannan et al. (1992) "Sonophoresis I. The Use of High Frequency Ultrasound to Enhance Transdermal Drug Delivery", Pharmaceutical Research 9(4), pp. 559-564.
Bommannan et al. (1992) "Sonophoresis II. Examination of the Mechanisms of Ultrasound-Enhanced Transdermal Drug Delivery", Pharmaceitcal Research 9(8), pp. 1043-1047.
Ishigaki, Y., et al. (1999). "Development and Characterization of a DNA Solar Dosimeter," Journal of Photochemistry and Photobiolgy. 50. pp. 184-188.
Gross, A. (1999). "Entering the Japanese Medical Device Market: The latest trends mean even better opportunities for foreign medical technology manufacturers," Medical Devicelink, Accessed: Dec. 15, 2001.
Gross, A., & Dyson, P. (1996). "Changing Regulatory Climate Improves Korean Market of U.S. Companies," Medical Device and Diagnostic Industry.
LeDoux, S.P., & Wilson, G.L. (2001). "Base Excision Repair of Mitochondrial DNA Damage in Mammalian Cells," Progress in Nucleic Acid Research and Molecular Biology, 66. pp. 273-284.
Turnbull, D., & Lightowlers, R. (2001). "Might Mammalian Mitochondria Merge?" Nature Medicine, 7(6). pp. 895-896.
Nakada, K., et al. (2001). "Inter-mitochondrial complementation: Mitochondria-specific system preventing mice from expression of disease phenotypes by mutant mtDNA," Nature Medicine, 7(8). pp. 934-940.
Vogel, W.F. (2001) "Collagen-receptor signaling in health and disease," European Journal of Dermatology, 11(6). pp. 506-514.
Curat, C., et al. (2001) "Mapping of eptiopes in discoidin domain receptor 1 critical for collagen binding," Journal of Biological Chemistry, 6(49).
Hou, G., Vogel. W., & Bendeck, M.P. (2001). "The discoidin domain receptor tyrosine kinase DDR1 in arierial wound repair," Journal of Clinical Investigation, 107(6). pp. 727-735.
Chin G.S., et al. (2000), "Cellular signaling by tyrosine phosphorylation in keloid and normal human dermal fibroblasts," Plastic Reconstructive Surgery, 106(7), pp, 1532-1540.
Weiner, H.L., et al, (2000), "Consistent and selective expression of the 11 human brain tumors," Neurosurgery, 47(6), pp 1400-1409.
Chin, G.S., et al. (2000). "Differential expression of receptor tyrosine kinases and Shc in fetal and adult rat fibroblasts: Toward defining scarless versus scarring fibroblast phenotypes," Plastic Reconstructive Surgery, 105(3). pp. 972-979.
Vogel, W., et al. (2000). "Discoidin domain receptor 1 is activated independently of beta 1 integrin," Journal of Biological Chemistry 275(8), pp. 5779-5784.
Vogel, W. (1999). "Discoidin domain receptors: Structural relations and functional implications," FASEB Journal, 13. pp. 77-82.
Norman, J.T., & Fine, L.G. (1999). "Progressive renal disease: Fibroblasts, extracellular matrix, and integrins," Experimental Nephrology, 7(2). pp. 167-177.
Shrivastava, A., et al. (1997). "An orphan receptor tyrosine kinase family whose members serve as non integrin collagen receptors," Molecular Cell, 1(1). pp. 25-34.
Vogel, W., et al. (1997). "The discoidin domain receptor tyrosine kinases are activated by collagen," Molecular Cell, 1 (1). pp. 13-23.
Sakuma, S., et al. (1996). "Receptor protein tyrosine kinase Ddr is up-regulated by p53 protein," FEBS Letters, 2. pp. 398, 165-169.
Hardell, L., et al. (2001). "Ionizing radiation, cellular telephones and the risk for brain tumors," European Journal of Cancer Prevention, 10(6). pp. 523-529.

Seishima, M., Oyama, Z., & Yamamura, M, (2002). "Cellular phone dermatitis," Archives of Dermatology, 138(2), pp. 272-273.
Di Carlo, A., et al, (2002), "Chronic electromagnetic field exposure decreases HSP70 levels and lowers cytoprotection," Journal of Cellular Biochemistry. 84(3). pp. 447-454.
French, P,W., et al, 2001 , "Mobile phones, heat shock proteins and cancer," Differentiation, 67(4-5). pp, 93-97.
Frumkin, H. et al. (2001). "Cellular phones and risk of brain tumors," CA: A Cancer Journal for Clinicians, 51(2). pp. 137-141.
Moustafa, Y.M., et al. (2001). "Effects of acute exposure to the radiofrequency fields of cellular phones on plasma lipid peroxide and antioxidase activities in human erythrocytes," Journal of Pharmaceutical and Biomedical Analysis, 26(4). pp. 605-608.
Chiladakis, J.A., et al. (2001). "In-vivo testing of digital cellular telephones in patients with implantable cardioverter-defibrillators," European Heart Journal, 22(15). pp. 1337-1342.
Santini, R., et al. (2001). "Symptoms reported by mobile cellular telephone users." Pathological Biology, 49(3). pp. 222-226.
Roti, J.L., et al. (2001). "Neoplastic transformation in C3H 10T(1/2) cells after exposure to 835.62 MHz FDMA and 847.74 CDMA radiations," Radiation Research, 155(1-2). pp. 239-247.
Wainwright, P. (2000). " Thermal effects of radiation from cellular telephones," Physics in Medicine and Biology, 152(3). pp. 293-302.
Adey, W.R., et al. (1999). "Spontaneous and nitrosourea-induced primary tumors of the central nervous system in Fischer 344 rats chronically exposed to 836 MHz modulated microwaves," Radiation Research, 152(3). pp. 293-302.
Robert, E. (1999). "Intrauterine effects of electromagnetic fields- (low frequency, mid-frequency RF, and microwave): A review of epidemiologic studies," Teratology, 59(4). pp. 292-298.
De Seze, R., Fabbro-Peray. P., & Miro, L. (1998), "GSM radiocellular telephones do not disturb the secre on of antepituitary hormones in humans," Bioelectromagnetics, 19(5). pp, 271-278.
Malyapa, R.S., et al, (1997). "Measurement of DNS damage after exposure to electromagnetic radiation in the cellular phone communication frequency band (835.62 and 847.74 MHz)," Radiation Research, 148(6). pp. 618-627.
Litovitz, T.A., et al. (1997), "Bioeffects induced by exposure to microwave are mitigated by superposition of ELF noise," Bioelectromagnetics, 18(6). pp. 422-430.
Omura, Y., & Losco, M. (1993), "Electro-magnetic fields in the home environment (color TV, computer monitor, microwave oven, cellular phone. etc) as potential contributing factors for the induction of oncogen C-fos Ab1, oncogen C-fos Ab2, integrin alpha 5 beta 1 and development of cancer, as well as effects of microwave on amino acid composition of food and living human brain," Acupuncture and Electro-Theraputics Research, 18(1). pp. 33-73.
Knave, B. (2001). "Electromagnetic fields and health outcomes," Annals Academy of Medicine Singapore, 30(5). pp. 489-493.
De Seze, R., et al. (1999). "Evaluations in humans of the effects of radiocellular telephones on the circadian patterns of melatonin secretion, a chronobiological rhythm marker," Journal of Pineal Research, 27(4). pp. 237-242.
Fluhr, J.W., et al. (1999). "In-vitro and in-vivo efficacy of zinc acetate against propionibacteria alone and in combination with erythromycin," Zentralbl Bakteriol, 289(4). pp. 445-456.
Itoh, Y., et al. (2001). "Photodynamic therapy of acne vulgaris with topical delta-a nolaevulinic acid and incoherent light in Japanese patients," British Journal of Dermatology, 144(3). pp. 575-579.
Lang, K., et al. (2001). "Aminolevulinic acid: Pharmacological profile and clinical indication," Expert Opinion on Drug Discovery, 10(6). pp. 1139-1156.
Ashmead, H.D. "The Need for Better Nutrition in our Food." Clearfield. Utah. USA. pp. 1-20.
Van Remmen, H. & Richardson, A. (2001), "Oxidative Damage to Mitochondria and Aging," Experimental Geology 36, pp. 957-968.
Rice, B.W., et al. (2001). "In Vivo Imaging of Light-emitting Probes," Journal of Biomedical Optics 6(4), pp. 432-440.
Moretti, M. (2001). "ICN Develops Integrated Skin Treatment Package," Aesthetic Buyers Guide Nov. 2001.

(56) References Cited

OTHER PUBLICATIONS

Neudecker, B.A., Stern. R., & Connolly, M.K. "Aberrant Serum Hyaluronan and Hyaluronidase Levels in Scleroderma." Department of Pathology and Dermatology, School of Medicine, University of California San Francisco.
Leyden, J., et al. (1999). "Finasteride in the Treatment of Men with Frontal Male Pattern Hair Loss," Journal of the American Academy of Dermatology 40(6). pp. 930-937.
Sommer, A.P. et al. (2001). "Biostimulatory Windows in Low-Intensity Laser Activation: Lasers, Scanners, and NASA's Light-Emitting Diode Array System," Journal of Clinical Laser Medicine and Surgery 19(1). pp. 29-33.
Troy, T. (2002). "Fluorescent Pulsed Light Makes Foray," Dermatology Times Jan. 2002.
Panteleyev, A., Jahoda, C., & Christiano, A. (2001). "Hair Follicle Predetermination," Journal of Cell Science 114. pp. 3419-3431.
Yoon, J.H., et al. (2000). "The DNA Damage Spectrum Produced by Simulated Sunlight," Academic Press, pp, 681-693.
Draper, B., et al. (2002). "MNPs and TIMP-1 are Differentially Expressed Between Acute Murine Excisional and Laser Wounds," Lasers in Surgery and Medicine 30, pp. 106-116.
Takemura et al.(1998), "Enhanced Interleukin 6 Production by Cultured Fibroblasts from Patients with Systemic Sclerosis in Response to Platelet Derived Growth," the Journal of Rheumatology, pp. 1534-1539. El.
Czuwara et al. (2001), "Differential regulation of transforming growth factor-8 receptors type I and Ii by platelet-derived growth factor in human dermal fibroblasts," British Journal of Dermatology, 569-575.
Loftsson et al. (1995), "Fatty acids from cod-liver oil as skin penetration enhancers," Die Pharmazie, pp. 271-773.
Stahl et al. (2000), "Carotenoids and carotenoids plus vitamin E protect against unitraviolet light-induced erythema in humans," the American Clinical Journal of Nutrition, pp. 795-798.
Gambichler et al. (2001), "Ultraviolet protection by summer textiles. Ultraviolet transmission measurements verified by termination of the minimal erythema dose with solar simulated radiation," British Journal of Dermatology, pp. 484-489.
Stahl et al. (2001), "Dietary Tomato Pasta Protects against Ultraviolet Light-Induced Erythema in Humans," Biochemical and Molecular Action of Nutrients Research Communication, pp. 1449-1451.
Lee et al. (2000), "Carotenoid Supplementation Reduces Erythema in Human Skin After Simulated Solar Radiation Exposure," Society of Experimental Biology and Medicine, pp. 170-174.
Moy et al. (2000), "Incresed Glycosaminolycans Production in Sclersoing Basal Cell Carcinoma-Derived Fibrolasts and Stimulation of Normal Skin Fibrolast Glycosaminoglycans Production by a Cytokine-Derived from Sclerosing Basal Cell Carcinoma," Dermatolgoic Surgery, pp. 1029-1035.
Takehara, K. (2000), "Grown regulation of skin fibroblasts," Journal of Dermatologial Science, pp. 70-74.
Loftsson, T. (1989), "Effect of choline esters and oleic acid on the penetration of acyclovir, estradiol, hydrocortisone, nitroglycerin, retinoic acid and trifluorothymidine across hairless mouse skin in vitro," Acta. Pharm. Nord., pp. 279-286.
Masson et. al, (2000), "Marine lipids for prodrugs, soft compounds and other pharmaceutical applications," Pharmazie, pp. 172-177.
Gross et al. (1978), "Comprehensive compilation of empirical ultrasonic properties of mammalian tissues," Journal of the Acoustical Society of America, pp. 423-457.
Fei et al. (1986), "Ultrasonic backscatter from bovine tissues: Varation with pathology," Journal of the Acoustical Society of America, pp. 166-172.
Fei, D and Shung, K. (1986), "Ultrasonic backscatter from bovine tissues," Journal of the Acoustical Society of America, pp. 871-876.
Chivers, R. and Parry R.(1978), "Ultrasonic velocity and attenuation in mammalian tissues," Journal of the Acoustical Society of America, pp. 940-954.

de Weerd et al. (2002), "Pathways for Energy transfer in the Core Light Harvesting Complexes CP43 and CP 47 of Photosystem II," Biophysical Journal, pp. 1586-1597.
Fluhr et al. (1999), "In-vitro and in-vivo Efficacy of Zinc Acetate against Propionibacteria Alone and in Combination with Erythromycin," Zent. bl. Bakerologie, pp. 445-456.
Lang et al. (2001), "Aminolevulinic acid: pharmacological profile and clinical indication," Expert Opinion Investigative Drugs, pp. 1139-1156.
Yakushevska et al. (2001), "Supermolecular organization of photosystem II and its associated light-harvesting antenna in Arabidopsis thalinana," European Journal of Biochemistry, pp. 6020-6028.
Polivka et al. (2002), "Carotenoid Si State in a Recombinant Light-Harvesting Complex of Photosystem II," Biochemistry, pp. 439-450.
Vander Meulen et al. (2002), "Calcium Depletion Modifies the Structure of the Photosystem II O2-Evolving Complex," Biochemistry, pp. 958-966.
Park et al. (2000), "Epidermal Growth (EGF) Antagonizes Transforming Growth Factor (TGF)-β1-Induced Collagen Lattice Contraction by Human Skin Fibroblasts," Biological and Pharmaceutical Bulletin, pp. 1517-1520.
Diffey et al. (2000), "In vitro assessment of the broad-spectrum ultraviolet protection of sunscreen products," Journal of the American Academy of Dermatology, pp. 1024-1035.
Zhu et al. (1997), "Photo-Irradiation Improved Functional Preservation of the Isolated Rat Heart," Lasers in Surgery and Medicine, pp. 332-339.
Yu et al. (1997), "Improvement of Host Response to Sepsis by Photobiomodulation," Lasers in Surgery and Medicine, pp. 262-268.
Shapiro, J and Price, V. (1998), "Hair Regrowth: Therapeutic Agents," Dermatologic Therapy, pp. 341-356.
El Sayed, S and Dyson, M. (1990), "Comparision of the Effect of Multiwavelength Light Produced by a Cluster of Semiconductor Diodes and of Each Individual Diode on mast Cell Number and Degranulation in Intact and Injured Skin," Lasers in Surgery and Medicine, pp. 559-568.
Huang et al. (2002), "Two-Photon Fluorescence Spectroscopy and Microscopy of NAD(P)H and Flavoprotein," Biophysical Journal, pp. 2811-2825.
Yamazaki et al. (1992), "Slecetive Chemical Modification of Amino Acid Residues in the Flavin Adrenie Dinucleotide Binding Site of Nadph-Ferredoxin Reductase," Internternational Journal of Biochemistry, pp. 223-228.
Andersson et al. (1998), "Autofluoresence of living cells," Journal of Microscopy. pp. 1-7.
Chen et al. (2002), "New Technology for Deep Light Distribution in Tissue for Phototherapy," The Cancer Journal, pp, 154-163,.
Baena-Gonzalez et al. (2001), "Cloroplast Transcription at Different Light Intensities, Glutathione-Mediated Phosphorylation of the Major RNA Polymerase Involved in Redox-Regulated Organellar Gene Expression," Plant Physiology, pp. 1044-1052.
Cheng, K. and Goldman R, (1998), "Electronic Field and Proliferation in a Dermal Wound Model: Cell Cycle Kinetics," Bioelectromagnetics, 68-74.
Stough et al. (2002), "Finasteride improves male pattern hair loss in a randomized study in indentical twins," European Journal of Dermatology, pp. 32-37.
Todd et al. (2001), "Electrical Stimulation of Transforming Growth Factor-β1 Secretion by Human Dermal Fibroblasts and the U937 Human Monocyctic Cell Line," pp. 693-701.
Unholzer, A and Korting, H. (2002), "High Frequency Ultrasound in the Evaluation of Pharmacological Effects on the Skin," Skin Pharmacology and Applied Skin Physiology, pp. 71-84.
Pelle et al. (2002), "Cigareete Smoke-Inducted Lipid Peroxidation in Human Skin and its Inhibition by Topically Applied Antioxidants," Skin Pharmacology and Applied Skin Physiology, pp. 63-68.
Garbaers et al. (2001), "Mössbauer study of iron centers in D1/D2/Cyt b 559 complexes isolated from photostem II of spinach," European Biophysics Journal, pp. 485-493.
O.Ishiawa et al. (1997), "Morphological and biochemical analyses on fibroblasts and self-produced collagens in a novel three dimensional culture," British Journal of Dermatology, pp. 6-11.

(56) References Cited

OTHER PUBLICATIONS

Harmon, C. and Nevins, T. (1994), Biophasic Effect of 1, 25-Dihyoxyvitamin D on Human Hair Follicle Growth and Hair Fiber Production in Whole Organ Cultures, Journal of Investigative Dermatology pp. 318-322.

Reiss, S. (2002), "Photodynamic Therapy' Reaching Beyond Cancer," Biophotonics International Journal, pp. 48-54.

Lahjomri et al, (1997), "Pulsed Photoacoustic Study of the Diffusion of Chromophores in Human Skin," Photochemistry and Photobiology, pp. 292-302.

Agramonte, A. (2001), "The Inside History of a Great Medical Discovery," Military Medicine, pp. 66-78.

Tsukahara et al, (2001). "Dirunal variation affects age-related profile in skin thickness," Journal of Cosmetic Science, pp, 391-397.

4 Ernst, E. and Huntley, A. (2000), "Tea Tree Oil: A system Review of Randomized Clinical Trials," Research in Complementary Medicine, pp. 17-20.

Masuda et al. (2002), "Biosynthesis and distribution of chlorophyll among the photosystems during recovery of the green alga *Dunaliella salina* from irradiance stress," Plant Physiology, pp. 603-614. (Abstract).

Joet et al. (2002), "Cyclic Electron Flow around Photosystem I in C(C) Plants. In Vivo Control byu the Redox State of Chloroplasts and Involvement of the NADH-Dehydroense Complex," pp. 760-769. (Abstract).

Christen et al. (2000), "Delayed Fluorescence emitted from light harvesting complex II and photosystem II of higher plants in the 100 ns-5 mircos time domain," FEBS Lett, pp. 103-106. (Abstract).

de Wijn et al. (2001), "Secondary stabilization reactions and proton-coupled electron transport in photosytem II investigated by electroluminescence and fluorescence spectroscopy," Biochemistry, pp. 5821-5834.

Hou et al. (2001), "Thermodynamics of electron transfer in oxygenic photosystem reaction centers; a pulsed photoacoustic study of electron transfer in photosystem I reveals a similarity to bacertial reaction centers in both volume change and entropy," Biochemistry, pp. 7109-7016.

Kemmatp, et al. (May 2001), "What Color is my LED?" Photonics Spectra.

Laakso, et al. (1997), "Pain Scores and Side Effects in Response to Low Level Laser Therapy (LLLT) for Myofascial Trigger Points", Laser Therapy 9:67-72.

Labbe et al., (1990), "Laser Phobioactivation Mechanisms: In Vitro Studies Using Ascorbic Acid Uptake and Hydroxyproline Formation as Biochemical Markers of Irradiation Response", Lasers in Surgery and Medicine 10, pp. 201-207.

Liberman et al. (1996), "Light Years Ahead", pp. 277-283.

Lieb, Linda, et al. (1992), "Topical Delivery Enhancement with Multilamellar Liposomes into Pilosebaceous Units: I. In Vitro Evaluation Using Fluorescent Techniques with the Hamster Ear Model", The Journal of Investigative Dermatology 99(1).

Li, Lingna ,et al. (1992), "Product-Delivering Liposomes Specifically Target Hair Follicles in Histocultured Intact Skin", In Vitro Cell Dev. Biol. 281, pp. 679-681.

Liu et al. (2002), "Inhibition of AP-1 Transcription Factor Causes Blockade of Multiple Signal Transduction Pathways and Inhibits Breast Cancer Growth", Oncogene 21:7680-7689.

Loevschall, (1994), "Effect of Low Level Diode Laser Irradiation of Human Oral Mucosa Fibroblasts in Vitro", Lasers in Surgery and Medicine 14, pp. 347-354.

Logdberg-Anderson et al. (1997), "Low Level Laser Therapy (LLLT) of Tendonitis and Myofascial Pains: A Randomized, Double-blind, Controlled Study", Laser Therapy 9:79-86.

Kloth, Luther, et al. (1996), "Promotion of Wound Healing with Electrical Stimulation", The Journal for Prevention and Healing Advances 9(5).

Coldman, M.F., et al. (1969), "Enhancement of Percutaneous Absorption by the Use of Volatile: Nonvolatile Systems as Vehicles", Journal of Pharmaceutical Sciences vol. 58, #9.

Hrnjak, M., et al. (Nov. 1995), "Stimulatory Effect of Low-Power Density He-Ne Laser Radiation on Human Fibroblast in Vitro", Vojnosanit Pregl. 52(6), pp. 539-546.

Callam, M. J., et al. (Jul. 1987) ,"A Controlled Trial of Weekly Ultrasound Therapy in Chronic Leg Ulceration", The Lancet, pp. 204-206.

Pogrel, M., et al. (1997) ,"Effects of Low-Energy Gallium-Aluminum-Arsenide Laser Irradiation on Cultured Fibroblasts and Keratincytes", Lasers in Surgery and Medicine 20, pp. 426-432.

Suzuki, M., et al. (1978), "Autoradiographic Study on Percutaneous Absorption of Several Oils Useful for Cosmetics", J. Soc. Cosmet Chem. 29, pp. 265-282.

Weiner, M., et al. (1994), "Liposomes: A Novel Topical Delivery System for Pharmaceutical and Cosmetic Applications", Journal of Drug Targeting 2, pp. 405-410.

Dyson, Mary (Sep. 1982), "Stimulation of Tissue Repair by Therapeutic Ultrasound", Infections in Surgery 1(2), pp. 37-44.

Dyson, Mary, et al. (Apr. 1978), "Stimulation of Tissue Repair by Ultrasound: A Survey of the Mechanisms Involved", Physiotherapy 64(4), pp. 105-108.

McDaniel (May 2001), "Nonablative Skin Rejuvenation—The Wave of the Future", Cosmetic Surgery Times.

McDaniel, D. H., et al. (1996), "Treatment Of Stretch Marks With the 585-nm Flashlamp-Pumped Pulsed Dye Laser", Dermatological 22(4), pp. 332-337.

Menezes et al. (Oct. 1998), "Non-Coherent Near Infrared Radiation Protects Normal Human Dermal Fibroblasts from Solar Ultraviolet Toxicity", The Journal of Investigative Dermatology 111(4):629-633.

Monfrecola, G., et al (1987), "Topical Hematoporphyrin Plus UVA for Treatment of Alopecia Areata", Photodermatology 4:305-306.

Lehman, P. et al. (1991), "Effects of Ultraviolet A and B on the Skin Barrier: A Functional Electron Microscopic and Lipid Biochemical Study", Photodermatol Photoimmunol Photomed. 8, pp. 129-134.

Morganti, P., et al. (1997), "Enhancing the Glycolic Acid Efficacy by Piezoelectric Vibrations," J. Appl. Cosmotol. vol. 15, pp. 147-159.

Singh, Parminder, et al. (1993), "Iotophoretic Transdermal Delivery of Salicylic Acid and Lidocaine to Local Subcutaneous Structures", Journal of Pharmaceutical Sciences 82(2), pp. 127-131.

Parrish et al. (1981), "Action Spectrum for Phototherapy of Psoriasis," Journal of Investigative Dermatology 76 (5):359-362.

De Deyne, Patrick G., et al. (711995), "In Vitro Effects of Therapeutic Ultrasound on the Nucleus of Human Fibroblasts", Physical Therapy 75(7), pp. 629-634.

Scheuplein, Robert ,et al. (1971), "Permeability of the Skin", Physiological Review, vol. 51, No. 4.

Polo, et al. (1999), "Role of Ground and Excited Singlet State Ozygen in the Red Light-Induced Stimulation of *Escherichia coli* Cell Growth", Biochemical and Biophysical Research Communications 257, pp. 753-758.

Potinen et al. (1996), "Comparative Effects of Exposure to Different Light Sources (He-Ne Laser, InGaAl Diode Laser, A Specific Type of Noncoherent LED) On Skin Blood Flow for the Head", Res. Int. J., vol. 21, pp. 105-118.

Brucks, Richard, et al. (1989), "The Effect of Ultrasound on the In Vitro Penetration of Ibuprofen Through Human Epidermis", Pharmaceutical Research 6(8), pp. 697-701.

Borelli, S. (1955), "Chlorophyll in the Treatment 1-27 of Acne Vulgaris", Dematologie, Venerologie, und Verwandte Gebiete 6(7), pp. 320-324.

Mordon, S., et al (1997), "Thermal Damage Assessment of Blood Vessels in a Hamster Skin Flap Model by Fluorescence Measurement of a Liposome-Dye System", Lasers in Surg. & Med. 20, pp. 131-141.

Mordon, S., et al. (1997), "Selective Laser Photocoagulation of Blood Vessets in a Hamater Skin Flip Model using a Specific ICG Formulation", Lasers Surg. Med. 21(4), pp. 365-373.

Sakurai et al. (2000), "Inhibitory effect of low-level laser irradiation on LPS-stimulated prostaglandin E2 production and cyclooxygnase-2 in human gingival fibroblasts", in Er. J. Oral. Sci., Issue 108: pp. 29-34.

Schindl et al. (Sep. 2000), "Low-Intensity Laser Therapy: A Review", Journal of Investigative Medicine, 48(5).

(56) References Cited

OTHER PUBLICATIONS

Schul et al. (2002), "Enhanced repair of cyclobutane pyrimidine dimers and improved UV resistance in photolyase transgenic mice", The European Molecular Biology Organization (EMBO) Journal 21(17):4719-4729.
ScienceDaily "2002 Nobel Price in Physiology or Medicine: Programmed Cell Death," dated Oct. 8, 2002, located at http://www.sciencedaily.com/releases/2002/10/021008064740.htm Retrieved On Oct. 24, 2007. (5 pages).
Shalita et al., (2001), "Acne PhotoClearing (APC) Using a Novel, High-Intensity, Enhanced, Narrow-Band, Blue Light Source", Clinical Application Notes 9(1).
Pinnell, Sheldon (1985), "Regulation of Collagen Biosynthesis of Ascorbic Acid: A Review" The Yale Journal of Biology and Medicine 58, pp. 553-559.
Tajima, Shingo, et al. (1996) "Ascorbic Acid Preferentially Enhances Type I and III Collagen Gene Transcription in Human Skin Fibroblasts", J. Dermatol. Sci. 11(3), pp. 250-253.
Skinner et al., (1996), "A Preliminary Study of the Effects of Laser Radiation on Collagen Metabolism in Cell Culture", Australian Dental Journal 41(3), pp. 188-192.
Sommer et al. (2001), "Biostimulatory Windows in Low-Intensity Laser Activation: Lasers, Scanners and NASA's Light Emitting Diode Array System", Journal of Clinical Laser Medicine & Surgery 19(1), pp. 29-33.
Sroka et al. (1999), "Effects on the Mitosis of Normal and Tumor Cells Induced by Light Treatment of Different Wavelengths", Lasers in Surgery and Medicine 25, pp. 263-271.
Sumlan et al., "A New Method to Improve Penetration Depth of Dyes into the Follicular Duct: Potential Application for Laser Hair Removal", J. Am. Acad. Dermatol. 41(2), pp. 172-175.
Melo, T. B. (1987), "Uptake of Protoporphyrin and Violet Light Photodestruction of Propionibacterium acnes", Journal of Biosciences 42(1-2), pp. 123-128.
Phillips, Charlotte, et al. (1994), "Effects of Ascorbic Acid on Profileration and Collagen Synthesis in Relation to the Donor Age of Human Dermal Fibroblasts", The Journal of Investigative Dermatology, vol. 103, No. 2.
Srinivasan, V., et al. (1989), "Transdermal Iontophoretic Drug Delivery: Mechanistic Analysis and Application to Polypeptide Delivery", Journal of Pharmaceutical Sciences 78(5).
Office Action dated Jun. 3, 2010 for Canadian Patent Application 2482934.
Response to Office Action dated Jun. 3, 2010 for Canadian Patent Application 2482934.
Office Action dated Feb. 1, 2011 for Canadian Patent application 2482934.
First Office Action dated Mar. 10, 2006 for Chinese Patent Application 03813556.6.
Response to First Office Action dated Mar. 10, 2006 for Chinese Patent Application 03813556.6.
Second Office Action dated May 23, 2008 for Chinese Patent Application 03813556.6.
Response to Second Office Action dated May 23, 2008 for Chinese Patent Application 03813556.6.
Rejection Decision dated Oct. 30, 2009 for Chinese Patent Application 03813556.6.
Response to Rejection Decision dated Oct. 30, 2009 for Chinese Patent Application 03813556.6.
Office Action dated Sep. 21, 2011 for Chinese Patent Application 03813556.6.
Response to Office Action dated Sep. 21, 2011 for Chinese Patent Application 03813556.6.
First Office Action dated Dec. 12, 2008 for Indian Patent Application 1590/KOLNP/2004.
Withdrawal Petition dated Nov. 20, 2009 for Indian Patent Application 1590/KOLNP/2004.
European Search Report dated Oct. 6, 2010 for European Application No. 04759316.5.
Office Action dated Feb. 2, 2011 for European Application No. 04759316.5.
Official Action dated Oct. 25, 2006 for Canadian Patent Application 2531099.
Office Action dated Dec. 7, 2010 for Japanese Patent Application 2006-509834.
Response to Office Action dated Dec. 7, 2010 for Japanese Patent Application 2006-509834.
Written Opinion of the International Search Authority dated Oct. 19, 2006 for Patent Application PCT/US04/24879.
Office Action dated Feb. 28, 2012 for Canadian Patent Application No. 2,533,129.
Response to Office Action dated Feb. 28, 2012 for Canadian Patent Application No. 2,533,129.
Office Action dated Jun. 17, 2011 for European Patent Application No. 04779826.9.
Response to Office Action dated Jun. 17, 2011 for European Patent Application No. 04779826.9.
First Office Action dated Jul. 15, 2009 for European Patent Application 04779826.9.
Response to First Office Action dated Jul. 15, 2009 for European Patent Application 04779826.9.
Office Action dated May 31, 2010 for Israeli Patent Application 173123.
Response to Office Action dated May 31, 2010 for Israeli Patent Application 173123.
Office Action dated Apr. 7, 2010 for Japanese Patent Application No. 2006-522123.
Response to Office Action dated Apr. 7, 2010 for Japanese Patent Application No. 2006-522123.
Office Action dated Apr. 28, 2011 for Korean Patent Application 10-2006-7002207.
Response to Office Action dated Apr. 28, 2011 for Korean Patent Application 10-2006-7002207.
Office Action dated Aug. 12, 2011 for Korean Patent Application 10-2006-7002207.
Response to Office Action dated Aug. 12, 2011 for Korean Patent Application 10-2006-7002207.
Response to Official Notification dated Dec. 3, 2008 for Israeli Patent Application 171311.
Response to Second Office Action dated Nov. 12, 2007 for Chinese Patent Application 200480012575.X.
First Statement of Proposed Amendments dated Oct. 27, 2005 for Australian Patent Application 2002326716.
Office Action dated May 16, 2010 for Israeli Patent Application 160505.
Response to Office Action dated May 16, 2010 for Israeli Patent Application 160505.
Decision of Rejection dated Dec. 1, 2008 for Japanese Patent Application 2003-522355.
Response to Official Action dated Sep. 3, 2007 for Mexican Patent Application 2004/001710.
Search Report dated Apr. 26, 2006 for European Patent Application 02792232.7.
Response to Office Action dated Jul. 2, 2007 for European Patent Application 02792232.7.
Office Action dated Jun. 22, 2009 for European Patent Application 02792232.7.
Response to Office Action dated Jun. 22, 2009 for European Patent Application 02792232.7.
Office Action dated Oct. 18, 2010 for European Patent Application 02792232.7.
Response to Office Action dated Oct. 18, 2010 for European Patent Application 02792232.7.
Office Action dated Oct. 10, 2012 for European Patent Application 02792232.7.
First Examination Report dated Jul. 12, 2007 for Indian Patent Application 620/KOLNP/2004.
Official Action dated Feb. 14, 2008 for Israeli Patent Application 161865.
Response to Official Action dated Feb. 14, 2008 for Israeli Patent Application 161865.

(56) References Cited

OTHER PUBLICATIONS

Office Action dated Sep. 15, 2010 for Israeli Patent Application 161865.
Response to Office Action dated Sep. 15, 2010 for Israeli Patent Application 161865.
Office Action dated May 14, 2008 for Japanese Patent Application 2003-541770.
Report of Final Decision of Refusal dated Feb. 6, 2009 for Japanese Patent Application 2003-541770.
Office Action dated Sep. 23, 2009 for Korean Patent Application 7007060/2004.
Response to Office Action dated Sep. 23, 2009 for Korean Patent Application 7007060/2004.
Office Action dated Jul. 27, 2010 for Korean Patent Application 7007060/2004.
Response to Office Action dated Jul. 27, 2010 for Korean Patent Application 700706012004.
Appeal Brief dated Oct. 26, 2010 for Korean Patent Application 7007060/2004.
Office Action dated Dec. 9, 2010 for Korean Patent Application 700706012004.
Response to Office Action dated Dec. 9, 2010 for Korean Patent Application 700706012004.
Office Action dated Jan. 17, 2012 for Korean Patent Application 70007060/2004.
Official Letter dated May 21, 2008 for Mexican Patent Application 20041004463.
Response to Official Letter dated May 21, 2008 for Mexican Patent Application 2004/004463.
Examination Report dated Mar. 13, 2006 for New Zealand Patent Application 533303.
Search Report dated May 22, 2008 for PCT Application No. PCT/US07102958.
Search Report dated May 27, 2008 for PCT Application No. PCT/US07105288.
Search Report dated Mar. 2, 2008 for PCT Application No. PCT/US07/05288.
Examiner's first report dated Aug. 5, 2010 for Australian Patent Application 2007212519.
Office Action dated Aug. 26, 2011 for European Patent Application 07763561.3.
Voluntary Amendment dated Dec. 4, 2008 for European Patent Application 07763561.3.
Search Report and Opinion dated Apr. 23, 2009 for European Patent Application 07763561.3.
First Examination Report dated Aug. 19, 2009 for European Patent Application 07763561.3.
Response to First Examination Report dated Aug. 19, 2009 for European Patent Application 07763561.3.
Office Action dated Mar. 21, 2012 for Japanese Patent Application 2008-557382.
Response to Office Action dated Mar. 21, 2012 for Japanese Patent Application 2008-557382.
Heikkila, H., Stubb, S., & Kiistala, U. (1996). "Nail growth measurement employing nail indentation—an experimental follow-up study of nail growth in situ," Clinical and Experimental Dermatology, 21(2). pp. 96-99.
Zimny, S., & Pfohl, M. (2005). "Healing times and prediction of wound healing in neuropathic diabetic foot ulcers: a prospective study," Experimental and Clinical Endocrinology & Diabetes, 113(2). pp. 90-93.
Martinez, D., et al. "Wound healing response of the med al collateral ligament during hindlimb unweighting in young rats."
Rosenburg, L. (2003). "Wound healing, growth factors," Emedicine.
Mitragotri, S. (2000). "Synergistic effect of enhancers for transdermal drug delivery," Pharmaceutical Research, 17(11). pp. 1354-1359.
Mitragotri, S., et al. (2000). "Analysis of ultrasonically extracted interstitial fluid as a predictor of blood g levels," Journal of Applied Physiology, 89(3). pp. 961-966.

Anvar, M.D., et al. (2000). "Vascular and stromal features in the skin of the lower limb in patients with critical limb ischaemia," European Journal of Vascular and Endovascular Surgery, 20(2). pp. 125-131.
Eichler, W., et al. (2000). "Changes of interstitial fluid volume in superficial tissues detected by a miniature ultrasound device," Journal of Applied Physiology, 89)1). pp. 359-363.
Mitragotri, S., et al, (2000), "Transdermal extraction of analytes using low-frequency ultrasound," Pharmaceutical Research, 17(4). pp, 466-470.
Moli. M., et al. (2000). "Two children with suspected primary vasculitis of messenteric vessels—a case report," Nihon Rinsho Meneki Gakkai Kaishi, 23(2). pp, 148-155.
Matrogotri, S. et al. (2000). "Synergistic effect of low-frequency ultrasound and sodium lauryl sulfate on transdermal transport," Journal of Pharmaceutical Science, 89(7). pp. 892-900.
Mitragotri, S., & Kost. J. (2000). "Low-frequency sonophoresis: A noninvasive method of drug delivery and diagnostics," Biotechnology in Progress, 16(3). pp. 488-492.
Taylor, B.K., et al. (2000). "Opioid inhibition of formalin-induced changes n. plasma extravasation and blood flow in rats," PAIN, 84(2-3). pp. 263-270.
Fang, J., et al. (1999). "Effect of low-frequency ultrasound on the in vitro percutaneous absorption of clobetasol 17-propionate," International Journal of Pharmaceutics, 191(1). pp. 33-42.
Shoab, S.S., et al. (1999). "Plasma VEGF as a marker of therapy in patients with chronic venous diseases with oral micronised flavonoid fraction- a pilot study," European Journal of Vascular and Endovascular Surgery, 18(4). pp. 334-338.
Meidan, V.M., et al. (1999). "Ultrasound -enhanced diffusion into coupling gel during phonophoresis of 5-fluorouracil," International Journal of Pharmaceutics, 185(2). pp. 205-213.
Terai, M., et al. (1999). "Vascular endothelial growth factor in acute Kawasaki disease," American Journal of Cardiology, 83(3). pp. 337-339.
Singer, A.J., et al. (1999). "The effects of low-frequenecy ulstrasound on *Staphylococcus epidermidis*," Current Microbiology, 38(3). pp. 194-196.
Foldvari, M.. et al. (1998). "Liposome encapsulated prostaglandin E1 in erectile dysfunction: Correlation in vitro delivery through foreskin and efficacy in patients," Urology, 52(5). pp. 838-843.
!Wu, J., et al. (1998), "Defects generated in human stratum corneum specimens by ultrasound," Ultrasound in Medicine and Biology. 24(5), pp. 705-710.
Liu, J., Lewis, TN., & Prausnitz. M.R. (1998) "Non-invasive assessment and control of ultrasound-mediated membrane permeabilization," Pharmaceutical Research. 15(6), pp. 918-924.
Pedder, V.V., et al, (1998) . "Rationale of noninvasive method of drug administration at the prelymphatic," MED TEKH, 2 pp. 18-23.
Sigfridsson et al. (1995),"Electrogenetic light reactions in photsystem I: resolution of electron-transfers rates between the iron-sulfer centers," Proc. National Acadamy of Science U.S.A., pp. 3456-3462, (Abstract).
Voigt et al. (2002), "Spectral Substructure and Excitonic Interactions in the Minor Photosystem II Antenna Complex CP29 Revealed by Nonlinear Polarization Spectroscopy in Frequency Domain." Biochemistry, pp. 3049-3056. (Abstract).
Dacher et al. (2001), "Combined NPLC-MS and HPLC-NMR on-line coupling for the separation and determination of lutein and zeaxanthin stereoisomers in spinach and in retina," Analytical Chemistry, pp. 667-674. (Abstract).
Varani et al. (2001), "Inhibition of type I procollagen synthesis by damages collagen in photoaged skin and by collagenase-degraded collagen in vitro," American Journal of Pathology, pp. 931-941. (Abstract).
Yu et al. (1997), "Photomodulation of oxidative metabolism and electron chain enzymes in rat liver mitochondria," Photochem. Photobiol., pp. 866-871. (Abstract).
Quan et al. (2002), "Connective tissue growth factor: expression in human skin in vivo and inhibition by ultraviolet radiation," Journal of Investigative Dermatology, pp. 402-408. (Abstract).
Boudjelal et al. (2002), "Retinoid Signaling Is Attenuated by Protassome-Mediated Degradation of Retinoid Receptors in Human Keratinocyte HaCaTCells," Exp. Cell. Res., pp. 130-137. (Abstract).

(56) References Cited

OTHER PUBLICATIONS

Loschinger et al, (1998), "Stimulation of protein kinase A activity and induced terminal differentiation of human skin fibroblasts in culture by low-frequency electromagnetic fields," Toxicol. Lett., pp. 369-76. (Abstract).
Bourguignon. GJ, and Bourguignon, LY, (1987), "Electric stimulation of protein and DNA synthesis in human fibroblasts," FASBERS J., pp. 398-402. (Abstract).
Bourguignon et al. (1989), "Electric stimulation of human fibroblasts causes an increase in Ca2+influx and the exposure of additional insulin receptors," Journal of Cellular Physiology, pp. 379-385. (Abstract).
Quan et al. (2001), "Ultraviolet irradiation blocks cellular responses to transforming growth factor-beta by down-regulating its type-II receptor and inducing Smad7." Journal of Biological Chemistry, pp. 25349-26356, (Abstract).
Neudecker, B.A., et al. (2004) "Abberant Serum Hyaluronan and Hyaluronidase Levels in Scleroderma," The British Journal of Dermatology pp. 469-476.
Formby, Bent, et al. (2002) "Lactate Stimulates Hyaluronan and CD44 Expression in Cultured Fibroblasts: the Warburg Effect Revisited," Experimental Cell Research May 15, 2002; 276(1): 24-31.
Stern, Robert. (2001) "Minireview on the Mammalian Hyaluronidases: Introductory Remarks" pub. by Elsevier Science B.V., Matrix Biology p. 497.
Csoka, Antonei, B. (2001) "Minireview The Six Hyaluronidase-like Genes in Human and Mouse Genomes" pub. by Elsevier Science B.V., Matrix Biology pp. 499-508.
Boh, Erin E. (2001) "Free Radicals and Aging Skin" Cosmetic Dermatology vol. 14 No. 12 Dec. 2001 pr. 37-40.
Lubart, R. et al. (1992) "Effect of Light on Calcium Transport in Bull Sperm Cells" Journal of Photochemuistry Photobiology B. Sep. 15, 1992; 15(4): 337-41.
Webster, Guy (2001) "Acne Pathogenesis & update on Therapy" Jujisawa Healthcare, Inc. Lectureship Series IN Dermatology [pamphlet] pp. 1-24.
Loschinger, Monika (1998) "Stimulation of Protein Kinase A Activity and Induced Terminal Differentiation of Human Skin Fibroblasts in Culture by Low-Frequency Electromagnetic Fields" Toxicol Lett. Aug. 1998: pp. 96-97: 369-76.
Bedi, Monika K. (2002) "Herba therapy in dermatology" Archives of Dermatology Feb. 2002 pp. 138(2): 232-42.
Yu, Wei, (1997) "Photomodulation of Oxidative Metabolism and electron Chain Enzymes in Rat Liver Mitochondria" Photochemistry and Photobiology. Dec. 1997; 66(6): 866-71.
Barber, James (2002) "Short communication: P680 What is it and Where is it?" Bioelectrochemistry, vol. 55, No. 1, Jan. 2002, pp. 135-138(4).
Matsuad, Tatsuru et al. (2002) "Biosynthes s and distribution of Chlorophyll Among the Photosystems During recovery of the Green Alga *Dunaliella salina* From Irradiance Stress" Plant Physiology. Feb. 2002; 128(2): 603-14.
De Mattei, M. et al. (2001) "Effect of Pusled Electromagnetic Fields on human Articular Chodrocyte Proliferation" Connective Tissue Research 2001; 42(4): 269-79.
Krishtalik, Ll et al. (2000) "Effects of Medium Polarization and Pre-Existing Field on Activation Energy of Enzymatic Charge-Transfer Reactions" Biochimica Biophysica Acta. Jul. 20, 2000; 1459(1): 88-105.
Edwards, AM, Silva, E. "Effect of Visible Light on Selected Enzymes, Vitamins and Amino Acids" Journal of Photochemistry Photobiology B. Oct. 2001; 63(1-3): 126-31.
Sommer, Andrei P. "Abstracts From the 1st International workshop on Nearfield Optical Analysis, Reisenberg, Germany, Nov., 2000" Journal of Clinical Laser Medicine & Surgery vol. 19 No. 2 2001.
Yano, K., Lawrence, B.F., & Detmar, M. (2001). "Control of hair growth and follicle size by VEGF-mediated angiogensis." The Journal of Clinical Investigation, 107(4), pp. 409-417.

Wei, Y.H., et al. (2001). "Mitochondrial theory of aging matures-Roles of mtDNA mutuation and oxidative stress in human aging." Chinese Medical Journal, 64, pp. 259-270.
Hoffman, J.W., et al (2004). "Myocardial reperfusion injury: Etiology, mechanisms, and therapies." The Journal of the American Society of Extra-Corporeal Technology, 36, pp. 391-411.
Chwirot, W.B. (1986). "New indications of possible role of DNA in ultraweak photon emission from biological systems." Journal of Plant Physiology, 122, pp. 81-86.
Albrecht-Buehler, G. (1994). "Cellular infrared detector appears to be contained in the centrosome." Cell Motility and the Cytoskeleton 27, pp. 262-271.
Kiang, J.G. (2004). "Inducible heat shock protein 70kD and inducible nitric oxide synthase in hemorrhage/resuscitation-induced injury." Cell Research, 14(6), pp. 450-459.
Yu, W., et al (1997). "Improvement of host response to sepsis by photobiomodulatio." Lasers in Surgery and Medicine, 21(3), pp. 262-268.
Byrnes, K.R., et al. (2004). "Photobiomodulation improves cutaneous wound healing in an animal model of type II diabetes." Photomedicine and Laser Surgery, 22(4), pp. 281-290.
Byrnes, K.R., et al. (2005). "Light promotes regeneration and functional recovery and alters the immune response after spinal cord injury." Lasers in Surgery and Medicine, Feb. 9, (online).
Wong-Riley, M.T., et al. (2005). "Photobiomodulation directly benefits primary neurons functionally inactive by toxins: role of cytochrome c oxidase." Journal of Biological Chemistry, 280(6), pp. 4761-4771.
El Hindi, T., et al. (2004). "Determination of the antioxidant capacity of an antioxidant combination using the fluoroscan assay in vitro and visualization of its effects using histological methods." Archives of Dermatological Research, 296(6), pp. 258-264.
Elmets, C.A., Vargas, A., & Oresajo, C. (1992). "Photoprotective effects of sunscreens in cosmetics on sunburn and Langerhans cell photodamage." Photodermatology, Photoimmunology, and Photomedicine, 9(3), pp. 113-120.
Stein, R. (2005). "Fat found to accelerate aging process." Washington Post, Jun. 14, 2005.
Block, G., et al. (2004). "Plasma-C reactive protein concentrations in active and passive smokers: influence of antioxidant supplementation." Journal of the American College of Nutrition, 23(2), pp. 141-147.
Noda, Y., et al. (2002). "Antioxidant activities of pomegranate fruit extract and its anthocyanindins: delphindin, cyaniding, and pelagronidin." Journal of Agricultural and Food Chemistry, 50(1), pp. 166-171.
Monaco, J.L. & Lawrence, W.T. (2003). "Acute wound healing an overview." Clinics in Plastic Surgery, 30, pp. 1-12.
Hinz, B., et al. (2001). "Apha-smooth muscle actin expression upregulates fibroblast contractile activity." Molecular Biology of the Cell, 12, pp. 2730-2741.
Azevedo, L.H., et al. (2005). "Evaluation of low intensity laser effects on the thyroid gland of male mice." Photomedicine and Laser Surgery, 23(6), pp. 567-570.
Tuby, H., Maltz, L., & Oron, U. (2006). "Modulations of VEGF and iNOS in the rat heart by low level laser therapy are associated with cardioprotection and enhanced angiogensis." Lasers in Surgery and Medicine, 38, pp. 682-688.
Fratelli, M., et al. (2005). "Gene expression in profiling reveals a signaling role of gluthathione in redox regulation." PNAS, 102(39), pp. 13998-14003.
Hymes, S.R., Strom, E.A., & Fife, C. (2006). "Radiation dermatitis: Clinical presentation, pathophysiology, and treatment 2006." Journal for the American Academy of Dermatology, 54, pp. 28-46.
Omura, Y. (2004). "Special sunrise & sunset solar energy stored papers and their clinical applications for intractable pain, circulatory disturbances & cancer: Comparison of Beneficial effects between special solar energy stored paper and quigong energy stored paper." Acupuncture & Electro-therapeutics, 29, pp. 1-42.
Stoica, E. & Enulescu, O. (1988). "Catecholamine response to light in migraine" Cephalalgia, 8, pp. 31-36.

(56) References Cited

OTHER PUBLICATIONS

Kowluru, R.A. (2005). "Diabetic retinopathy: mitochondrial dysfunction and retinal capillary cell death." Antioxidants & Redox Signaling, 7(11,12), pp. 1581-1587.
McDaniel, D., et al. (1998). "Body contouring: A preliminary report on the use of the silhouette® device for treating cellulite." Aesthetic Surgery Journal, 18(3), pp. 177-182.
Noton, D. (2000). "Migraine and photic stimulation: Report on a survey of migraineurs using flickering light therapy." Complementary Therapies in Nursing & Midwifery, 6, pp. 138-142.
Alstadhaug, K.B., Salvesen, R., & Bekkelund, S.I. (2005). "Seasonal variation in migraine." Cephalalgiai, 25, pp. 811-816.
Claustrat, B., et al. (2004). "Melatonin secretion is supersensitive to light in migraine." Cephalalgia, 24, pp. 128-133.
Passache, G., et al. (2000). "Mitochondria of retinal muller (glial) cells: the effects of aging and of application of free radical scavengers." Opthalmic Research, 32, pp. 229-236.
Liang, F.Q. & Godley, B.F. (2003). "Oxidative stress-induced mitochondrial DNA damage in human retinal pigment epithelial cells: A possible mechanism for RPE aging and age-related macular degeneration." Experimental Eye Research, 76, pp. 397-403.
Anderson, D.J., et al. (1997). "Preliminary trial of photic stimulation for premenstrual syndrome." Journal of Obstetrics and Gynaecology, 17(1), pp. 76-79.
Main, A., et al. (2000). "The wavelength of light causing photophobia in migraine and tension-type headache between attacks." Headache, 40, pp. 194-199.
Eells, J.T. et al. (2004). "Mitochondrial signal transduction in accelerated wound and retinal healing by near-infrared light therapy." Mitochondrion, 4, pp. 559-567.
"Thiol" From Wikipedia p. http://en.wikipedia.org/wiki/Thiol Accessed: May 6, 2007.
"Disulfide Bond" From Wikipedia page: http://en.wikipedia.org/wiki/Disulfide_bond Accessed: May 6, 2007.
"Permanent Wave" From Wikipedia page: http://en.wikipedia.org/wiki/Permanent_wave Accessed: May 6, 2007.
Martin, K. (2007). "Infrared and ramen studies of skin and hair: A review of cosmetic spectroscopy." The Internet Journal of Vibrational Spectroscopy, 3(2), online Accessed: Apr. 24, 2007.
Non-Final Rejection dated Sep. 22, 2009 for U.S. Appl. No. 11/116,434.
Response to Non-Final Rejection dated Sep. 22, 2009 for U.S. Appl. No. 11/116,434.
Final Office Action dated Sep. 15, 2010 for U.S. Appl. No. 11/116,434.
Response to Final Office Action dated Sep. 15, 2010 for U.S. Appl. No. 11/116,434.
Advisory Action dated Dec. 22, 2010 for U.S. Appl. No. 11/116,434.
Appeal Brief dated Aug. 15, 2011 for U.S. Appl. No. 11/116,434.
Amendment to Miscellaneous Action dated Aug. 24, 2005 for U.S. Appl. No. 09/876,157.
Office Action dated Mar. 30, 2011 for U.S. Appl. No. 12/550,464.
Office Action dated Oct. 28, 2011 for U.S. Appl. No. 12/550,464.
Final Office Action dated May 29, 2012 for U.S. Appl. No. 12/550,464.
Response to Final Office Action dated May 29, 2012 for U.S. Appl. No. 12/550,464.
Notice of Restriction dated Mar. 29, 2006 for U.S. Appl. No. 10/665,390.
Response to Restriction dated Mar. 29, 2006 for U.S. Appl. No. 10/665,390.
Non Final Rejection dated Aug. 21, 2006 for U.S. Appl. No. 10/665,390.
Non Final Rejection dated Jan. 5, 2006 for U.S. Appl. No. 10/903,483.
Amendment to Non-Final Rejection dated Jan. 5, 2006 for U.S. Appl. No. 10/903,483.
Non Final Rejection dated Sep. 25, 2006 for U.S. Appl. No. 10/903,483.
Amendment to Non-Final Rejection dated Sep. 25, 2006 for U.S. Appl. No. 10/903,483.
Final Office Action dated Jun. 14, 2007 for U.S. Appl. No. 10/903,483.
Appeal Brief filed Jan. 28, 2008 for U.S. Appl. No. 10/903,483.
Non Final Rejection dated May 22, 2008 directed towards U.S. Appl. No. 10/903,483.
Non Final Rejection dated Jul. 18, 2007 for U.S. Appl. No. 11/205,316.
Amendment to Non-Final Rejection dated Jul. 18, 2007 for U.S. Appl. No. 11/205,316.
Final Rejection dated Jun. 9, 2008 for U.S. Appl. No. 11/205,316.
Non Final Rejection dated Oct. 19, 2007 for U.S. Appl. No. 11/272,042.
Amendment to Non-Final Rejection dated Oct. 19, 2007 for U.S. Appl. No. 11/272,042.
Final Rejection dated Jun. 6, 2008 for U.S. Appl. No. 11/272,042.
Non-Final Rejection dated Jun. 8, 2010 for U.S. Appl. No. 12/583,562.
Amendment to Non-Final Rejection dated Jun. 8, 2010 for U.S. Appl. No. 12/583,562.
Official Notification dated Dec. 3, 2008 for Israeli Patent Application No. 171311.
Official Notification dated Nov. 19, 2009 for Israeli Patent Application No. 171311.
Response to Official Notification dated Nov. 19, 2009 for Israeli Patent Application No. 171311.
First Office Action dated Mar. 10, 2006 for Chinese Patent Application No. 200480012575.X.
Response to First Office Action dated Mar. 10, 2006 for Chinese Patent Application No. 200480012575A.
Second Office Action dated Nov. 2, 2007 for Chinese Patent Application No. 200480012575.X.
Notice of Reexamination dated Jul. 27, 2010 for Chinese Patent Application No. 200480012575.X.
Response to Notice of Reexamination dated Jul. 27, 2010 for Chinese Patent Application No. 200480012575A.
Official Notification regarding clarification of claims dated Sep. 19, 2002 for PCT Patent Application No. PCT/US02/26627.
Request for Rectification of Obvious Errors in the International Patent Application and Submission of Request to Record Change of Agent's Address dated Sep. 27, 2002 for PCT Patent Application No. PCT/US02/26627.
International Search Report dated May 16, 2003 for PCT Patent Application No. PCT/US02/26627.
International Search Report dated May 8, 2003 for PCT Patent Application No. PCT/US02/35839.
International Preliminary Examination Report dated Oct. 7, 2003 for PCT Patent Application No. PCT/US02/35839.
Examiner's Report dated Mar. 22, 2007 for Australian Patent Application No. 2002326716.
Office Action dated Aug. 2, 2006 for Canadian Patent Application No. 2457590.
Response to Office Action dated Aug. 2, 2006 for Canadian Patent Application No. 2457590.
Office Action dated Apr. 30, 2007 for Canadian Patent Application No. 2457590.
Response and Amendment to Office Action dated Apr. 30, 2007 for Canadian Patent Application No. 2457590.
Office Action dated Jan. 31, 2008 for Canadian Patent Application No. 2457590.
Request for Reinstatement for Failure to Respond to Office Action dated Jan. 31, 2008 for Canadian Patent Application No. 2457590.
Office Action dated Feb. 6, 2013 for Japanese Patent Application 2008-557382.
Invitation to Correct defects dated Jul. 22, 2002 for Patent Application PCT/US02/20706.
Response to Correct defects dated Jul. 22, 2002 for Patent Application PCT/US02/20706.
Written Opinion dated Jul. 31, 2003 for Patent Application PCT/US02/20706.
Response to Written Opinion dated Jul. 31, 2003 for Patent Application PCT/US02120706.

(56) References Cited

OTHER PUBLICATIONS

Preliminary Examination Report dated Oct. 27, 2005 for Patent Application PCT/US02/20706.
International Search Report dated Aug. 11, 2003 for Patent Application PCT/US03/10509.
Preliminary Examination Report dated Jun. 17, 2004 for Patent Application PCT/US03/10509.
Official Action dated Jul. 28, 2010 for Israeli Patent Application 159579.
Official Action dated Sep. 8, 2008 for Israeli Patent Application 159579.
Response to Official Action dated Sep. 8, 2008 for Israeli Patent Application 159579.
Voluntary Amendment dated Apr. 19, 2006 for Canadian Patent Application 2452408.
Office Action dated Jun. 2, 2006 for Canadian Patent Application 2452408.
Response to Office Action dated Jun. 2, 2006 for Canadian Patent Application 2452408.
Office Action dated Mar. 2, 2007 for Canadian Patent Application 2452408.
Response to Office Action dated Mar. 2, 2007 for Canadian Patent Application 2452408.
Office Action dated Jan. 31, 2008 for Canadian Patent Application 2452408.
Response to Office Action dated Jan. 31, 2008 for Canadian Patent Application 2452408.
Office Action dated Nov. 10, 2008 for Korean Patent Application 7017182/2003.
Notices for Reasons of Rejection dated Mar. 26, 2008 for Japanese Patent Application 2003-508231.
Amendment dated Jul. 25, 2008 for Japanese Patent Application 2003-508231.
Examination Report dated Feb. 22, 2008 for New Zealand Patent Application 530600.
Response to Examination Report dated Feb. 22, 2008 for New Zealand Patent Application 530600.
Examination Report dated Aug. 20, 2008 for New Zealand Patent Application 530600.
Second Official Letter dated Jul. 27, 2007 for Mexican Patent Application 2004/000187.
Response to Second Official Letter dated Jul. 27, 2007 for Mexican Patent Application 2004/000187.
Third Official Letter dated Jan. 3, 2008 for Mexican Patent Application 2004/000187.
Response to Third Official Letter dated Jan. 3, 2008 for Mexican Patent Application 2004/000187.
Office Action dated Mar. 21, 2008 for Chinese Patent Application 02816794.5.
Response to Office Action dated Mar. 21, 2008 for Chinese Patent Application 02816794.5.
Second Office Action dated Jul. 22, 2009 for Chinese Patent Application 02816794.5.
Response to Second Office Action dated Jul. 22, 2009 for Chinese Patent Application 02816794.5.
Third Office Action dated Jan. 5, 2010 for Chinese Patent Application 02816794.5.
Response to Third Office Action dated Jan. 5, 2010 for Chinese Patent Application 02816794.5.
First Examination Report dated Feb. 8, 2007 for European Patent Application 02749720.
Response to First Examination Report dated Feb. 8, 2007 for European Patent Application 02749720.
First Statement of Proposed Amendments dated Feb. 17, 2006 for Australian Patent Application 2003220671.
Examiner's First Report dated Oct. 4, 2007 for Australian Patent Application 2003220671.
Voluntary Amendment dated Feb. 27, 2007 for Canadian Patent Application 2482934.
Office Action dated Jun. 15, 2007 for Canadian Patent Application 2482934.
Response to Office Action dated Jun. 15, 2007 for Canadian Patent Application 2482934.
Office Action dated Feb. 21, 2008 for Canadian Patent Application 2482934.
Response to Office Action dated Feb. 21, 2008 for Canadian Patent Application 2482934.
Office Action dated Oct. 17, 2008 for Canadian Patent Application 2482934.
Response to Office Action dated Oct. 17, 2008 for Canadian Patent Application 2482934.
De Bie, R., et al. (1998). "Low-level laser therapy in ankle sprains: A randomized clinical trial," Archives of Physical Medication and Rehabilitation, 79, pp. 1415-1420.
Kostenyuk, I., Oh, B.J., & So, S. (1999). "Induction of early flowering in cymbidium niveo-marginatum mak in vitro." Plant Cell Reports, 19(1) (abstract).
Schindl, A, et al. (1999) "Diabetic neuropathic foot ulcer: Successful treatment by low-intensity laser therapy." Dermatology, 198(3), pp. 314-316.
Schindl, A., et al. (1999) "Increased dermal angiogensis after low-intensity laser therapy for a chronic radiation ulcer determined by a video measuring system." Journal of the American Academy of Dermatology, 40(3), pp. 481-484.
Schindl, A, et al. (1999) "Low-intensity laser therapy is an effective treatment for recurrent herpes simplex infection. Results from a randomized double-blind placebo-controlled study." Journal of Investigative Dermatology, 113(2), pp. 221-223.
Schindl, A., et al. (1997) "Successful treatment of a persistent radiation ulcer by low power laser therapy," Journal of the American Academy of Dermatology, 37(4), pp. 646-648.
Schindl, M., et al. (1999) "Induction of complete wound healing in recalcitrant ulcers by low-intensity laser irradiation depends on ulcer cause and size." Photodermatology, Photoimmunology, and Photomedicine, 15(1), pp. 18-21.
Zugaro, A., et al. (1992) "Applicazione del laser infrarosso a colture in vitro di fibroblasti: efftii del parametro tempo di esposizione." Annali Italiani di Chirurgia, 63(2), pp. 193-195.
Srinivasan, V., et al. (1990), "Ionotphoresis of Polypeptides: Effect of Ethanol Pretreatment of Human Skin", Journal of Pharmaceutical Sciences 79(7), pp. 588-591.
Van Breugel et al. (1992), "Power Density and Exposure Time of He-Ne Laser Irradiation are More Important than Total Energy Dose in Photo-Biomodulation of Human Fibroblasts in Vitro", Lasers in Surgery and Medicine 12, pp. 528-537.
Vreman et al. (Nov. 1998), "Light-Emitting Diodes: A Novel Light Source for Phototherapy", vol. 44, Issue 5, pp. 804-809.
Vuillaume, et al. (2001), "Real Time RT-PCR Shows Correlation between Retinoid-Induced Apoptosis and NGF-R mRNA Levels", Biochemical and Biophysical Research Communications 289(3):647-652.
Harvey, W., et al. (1975), "The Stimulation of Protein Synthesis in Human Fibroblasts by Therapeutic Ultrasound," Rheumatology and Rehabilitation 14, 237.
Yu, W., et al. (1997), "Effects of Photostimulation on Wound Healing in Diabetic Mice", Lasers in Surgery and Medicine, 20(1), pp. 56-63.
Webb, et al., (1998), "Stimulatory Effect of 660 nm Low Level Laser Energy on Hypertrophic Scar-derived Fibroblasts: Possible Mechanisms for Increase in Cell Counts", Lasers in Surgery and Medicine 22, pp. 294-301.
Yu, Wei, et al. (1997), "Improvement of Host Response to Sepsis by Photobiomodulation", Lasers in Surgery and Medicine 21, pp. 262-268.
Wei, Li-Na (2004), "Retinoids and Receptor Interacting Protein 140 (RIP140) in Gene Regulation", Current Medicinal Chemistry 11(12):1527-1532.
Westerhof et al., "Treatment of Vitiligo with UV-B Radiation vs Topical Psoralen Plus UV-A", Arch Dermatol, vol. 133, Dec. 1997, pp. 1525-1528.
Whelan et al., "NASA Light Emitting Diode Medical Applications From Deep Space to Deep Sea", CP552, Space Technology and Applications International Forum 2001, p. 35-45.

(56) References Cited

OTHER PUBLICATIONS

Ritschel, Wolfgang, et al. (1989), "Percutaneous Absorption of Coumarin, Griseofulvin and Propranolol Across Human Scalp and Abdominal Skin", Meth and Find Exp. Clin. Pharmacol. 11(10), pp. 643-646.
Joachims, Z. et al. (1987), "Noise-Induced Hearing Loss in Humans as a Function of Serum Mg Concentration", Magnesium Bulletin No. 3, pp. 130-131.
Zelickson, et al. (1999), "Pulsed Dye Laser Therapy for Sun Damaged Skin", Lasers in Surgery and Medicine 25, pp. 229-236.
Goldman, Erik L. (1011999), "FotoFacial is a Pulsed Light Patient Pleaser", Skin and Allergy News, p. 34.
Newman Joseph T., et al. (Aug. 1992), "Hydrocortisone Phonophoresis, A Literature Review", Journal of the American Podiatric Medical Association, vol. 82, No. 8, 432-435.
Mitragotri, Samir, et al. (Aug. 11, 1995), "Ultrasound-Mediated Transdermal Protein Delivery", Science, vol. 269, pp. 850-852.
Office Action dated Jun. 20, 2013 for U.S. Appl. No. 12/583,578.
Response to Final Office Action dated Dec. 3, 2012 for U.S. Appl. No. 12/550,799.
European Office Action dated Jul. 21, 2008, directed to EP Application No. 02761449.4,.
European Search Report dated Sep. 16, 2005, directed to EP Application No. 02761449.4.
Third-Party Observations dated Sep. 12, 2007, directed to EP Application No. 02749720.5.
International Preliminary Examination Report dated Aug. 6, 2004 directed toward Patent Application PCT/US02/26627.
Office Action dated May 16, 2013 directed towards European Patent Application No. 04779826.9.
Office Action dated Nov. 16, 2012 directed towards Chinese Patent Application 201110210275.4.
Search Report dated Oct. 6, 2010 directed towards European Patent Application 07752016.1.
Application to Amend a Complete Specification dated Jul. 24, 2012 directed towards South African Patent Application 2004/1528.
Response to Office Action dated Jan. 17, 2012 for Korean Patent Application 70007060/2004.
Response to Examiner's First Report dated Aug. 5, 2010 for Australian Patent Application 2007212519.
Office Action dated Feb. 29, 2012 for Japanese Patent Application 2008-553383.
Response to Office Action dated Feb. 29, 2012 for Japanese Patent Application 2008-553383.
Official Letter dated Nov. 17, 2006 for Mexican Patent Application 20041000187.
Written Opinion of the International Search Authority dated Apr. 12, 2005 for Patent Application PCT/US04/10915.
Office Action dated May 11, 2010 for Japanese Patent Application 2006-509834.
Response to Office Action dated May 11, 2010 for Japanese Patent Application 2006-509834.
Office Action dated Feb. 25, 2013 for Japanese Patent Application 2008-553383.
Response to Office Action dated Feb. 22, 2012 for Japanese Patent Application 2009-236857.
Stables, G. I., et al. (1995), "Photodynamic Therapy", Cancer Treatment Reviews, vol. 21, pp. 311-323.
Katsumi, Toichiro A., et al. (1996), "Photodynamic Therapy With a Diode Laser for Implanted Fibrosarcoma in Mice Employing Mono-L-Aspartyl Chlorin E6", Photochemistry and Photobiology, 64(4), pp. 671-675.
J. Pospisilova et al. (1977) "Ultrasonic Effect on Collagen Synthesis and Deposition in Different Localized Experimental Granulomas," Acta Chirurgiae Plasticae 19, pp. 148-157.
Doan et al, (1999), "In Vitro Effects of Therapeutic Ultrasound on Cell Proliferation, Protein Synthesis, and Cytokin Production by Human Fibrosblasts, Osteoblasts, and Monocytes" J. Oral Maxillofac Surg. 57, pp. 409-419.
Suzuki, M., et al. (May 1978), "Autoradiographic Study on Percutaneous Absorption of Several Oils Useful for Cosmetics", J. Soc, Cosmet. Chem., 29, 265-282.
Decision of Rejection dated Feb. 2, 2009 for Japanese Patent Application 2003-508231.
US Office Action dated Sep. 13, 2013, issued in related U.S. Appl. No. 12/550,749 (client abandoned application Sep. 25, 2013; no response will be filed).
EP Office Action dated Oct. 2, 2013 issued in related EP patent application No. 02792232.7 (no response filed yet).

* cited by examiner

Fig. 1

PROCESS FOR TREATMENT OF PSORIASIS

RELATED APPLICATION

This application is a continuation of U.S. application Ser. No. 09/819,083, filed Feb. 15, 2001, which is a divisional application of U.S. patent application Ser. No. 09/203,178, filed on Nov. 30, 1998.

FIELD OF THE INVENTION

The present invention generally relates to a system for the reduction, elimination or stimulation of hair growth in mammalian skin.

BACKGROUND OF THE INVENTION

There are several known techniques for attempting to reduce, eliminate or stimulate hair growth in human skin. A few of these known techniques are scientifically proven and widely accepted as effective. However, their degree of efficacy varies greatly.

There are several processes which may be used for producing preferential damage of the hair. In one process the target may be natural melanin pigment in the hair shaft and surrounding supporting tissues. In another process the target may be an external chromophore or contaminant. Most of these processes tend to damage the hair, either by producing heat or by photo-acoustical shock waves. These known processes have varying degrees of effectiveness, but require multiple treatments and, in their current form, produce only partial permanent hair reduction.

In recent years the use of light sources to reduce or eliminate unwanted hair growth has been developed. One known technique selects a wavelength of laser light that is well-absorbed by the naturally occurring "native" pigments in the hair shaft (and perhaps some pigment in parts of the hair duct or hair follicle cells).

Another known technique uses a short pulsed laser to produce a wavelength that may be absorbed by a "foreign" material or "skin contaminant".

Aspects of this technique are described, for example, in U.S. Pat. Nos. 5,423,803, 5,817,089, 5,425,728, 5,226,907, and 5,752,949, all of which are incorporated by reference. This contaminant may be applied directly onto the skin and may be introduced into the empty space surrounding the hair shaft. One contaminant that has been used is carbon graphite in particulate form. The graphite particles have a diameter that is small enough to enable the particles to drop from the surface of the skin into the free empty spaces between the duct and the hair shaft. The energy from a laser may then interact with the contaminant particles. This causes injury to surrounding tissues whose function is to support the growth of the hair shaft. This tends to reduce or eliminate hair growth.

These contaminant particles are not physically incorporated into the hair shaft or into the surrounding hair follicle, hair bulge or hair duct cells. Nor do these contaminant particles chemically, immunologically, biologically or otherwise interact, react or complex with the hair shafts or tissue cells. The contaminant particles simply physically occupy the space surrounding the hair shaft.

Another known hair removal technique is to use a pulsed electromagnetic radiation source to produce a wavelength that may be absorbed by hair, as described, for example, in U.S. Pat. No. 5,683,380, which is incorporated by reference.

There are problems with present light and laser hair removal techniques. Known melanin targeting systems work reasonably well and are reasonably safe only when the color of the hair is very dark and when the skin is very light and not tanned. Virtually all light sources which tend to target melanin are also inherently absorbed by the overlying and surrounding skin. At present, these light sources cannot be safely used at optimal very high power settings for people with darker skin or even people with a dark tan.

Dying the hair allows increased damage to the hair target, helps confine damage to the hair target, and enables the use of power settings that are not so high as to damage surrounding and overlying skin. Treatments which target melanin inherently do not work well on light hair, since there is not enough natural pigment to absorb enough energy to damage hair even if the power is quite high. Using hair dye enables this obstacle to be overcome.

A known hair removal process which uses a 1064 nm laser to produce a wavelength that may be absorbed by a skin contaminant appears to be safe on all skin colors, including darker skin colors. However, this safety is a consequence of there being very little melanin absorption. It is therefore necessary to add graphite particles in oil contaminant lotion before laser treatment. This graphite particle lotion does not enter into the hair shaft itself. Instead, the graphite lotion tends to occupy empty spaces surrounding the hair shaft as it sits in the hair duct. This presents a problem. Either an insufficient or sub-optimal number of graphite particles penetrate into the hair duct, or an insufficient amount of damage is caused by the graphite particles. Consequently, many treatments tend to be required before an acceptable result is achieved.

SUMMARY OF THE INVENTION

The present invention enables the safe treatment of virtually all hair colors (including light hair) on virtually all skin colors (including light, untanned skin).

The present invention may be advantageously used with virtually any laser or light mediated hair removal device or process. The present invention tends to enhance damage to unwanted hair without significantly increasing adverse side effects or compromising safety. The present invention enables the use of existing light sources, by selecting a dye which is well absorbed by that light source.

The present invention encompasses all dyes or agents which may, by any mechanism, be attached or incorporated into the hair shaft or the hair duct cells or any part of the hair follicle cells or cells of the supporting tissues, including blood vessels supplying the hair follicle. These agents, and their breakdown products, are preferably non-toxic. Each agent may be appropriately matched to a corresponding light source.

The present invention may be used in conjunction with known laser or light sources. The present invention, in a preferred embodiment, tends to enhance laser or light activated hair removal. The present invention encompasses using one process to treat hair, and then going back over the area (or simultaneously) treating with two different light sources or simultaneously treating with single or multiple sources.

The present invention, in a preferred embodiment, is able to enhance virtually any hair removal process. Enhancement may occur, for example, by enabling more hair to be removed, or by eliminating hair for a longer period of time, or by increasing the probability (or percentage) of hairs that are permanently destroyed.

BRIEF DESCRIPTION OF THE DRAWINGS

A detailed description of a preferred embodiment of the present invention will be made with reference to the accompanying drawings.

Figure 1:
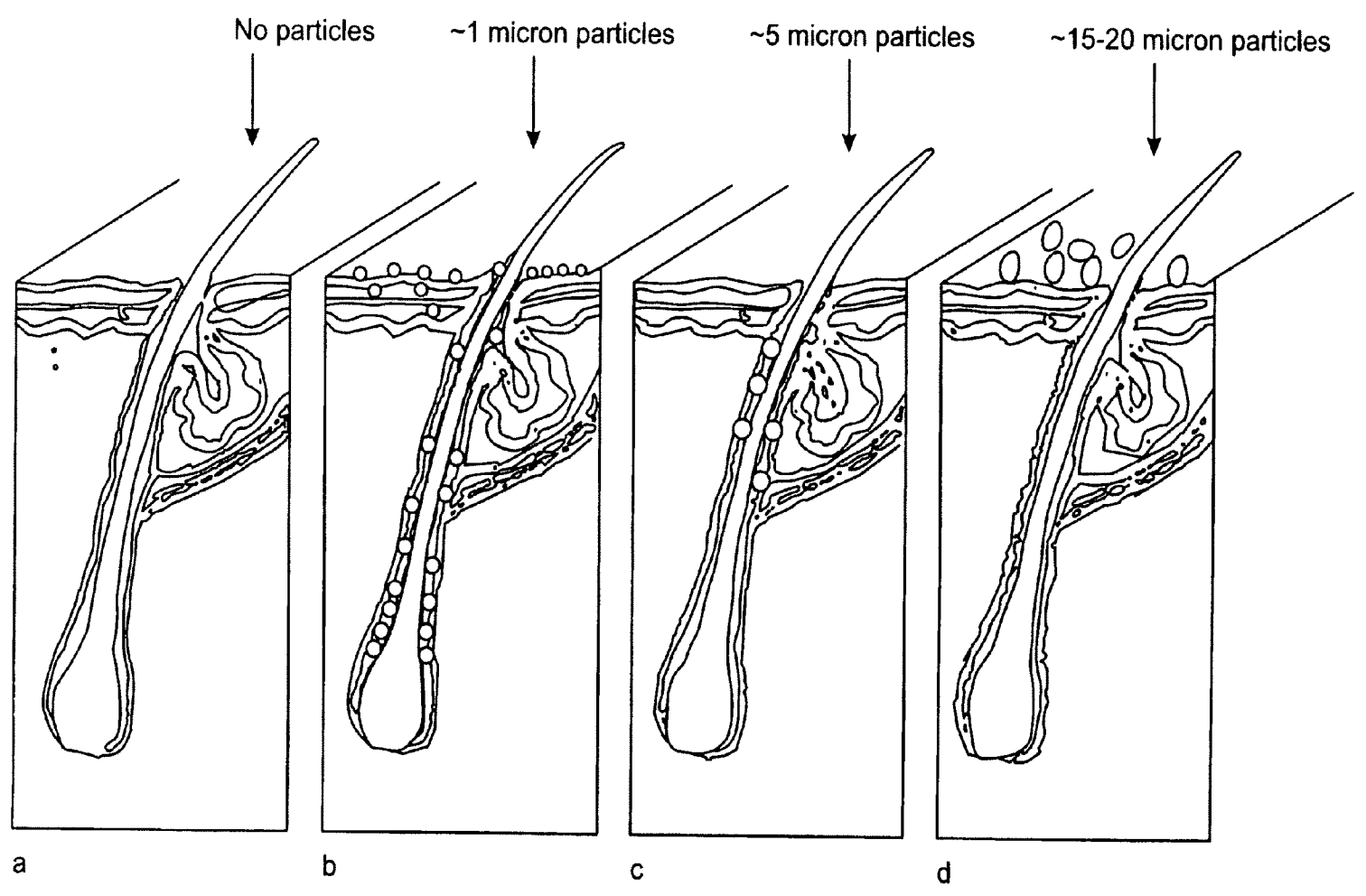

FIG. 1a illustrates an example of a hair duct and sebaceous glands without any particles being present.

FIG. 1b illustrates an example of a distribution of particles having an average diameter of about one micron in a hair duct and sebaceous glands.

FIG. 1c illustrates an example of a distribution of particles having an average diameter of about five microns in a hair duct and sebaceous glands.

FIG. 1d illustrates an example of a distribution of particles having an average diameter of about fifteen to twenty microns in a hair duct and sebaceous glands.

DETAILED DESCRIPTION OF THE PREFERRED EMBODIMENTS

Figure 2:
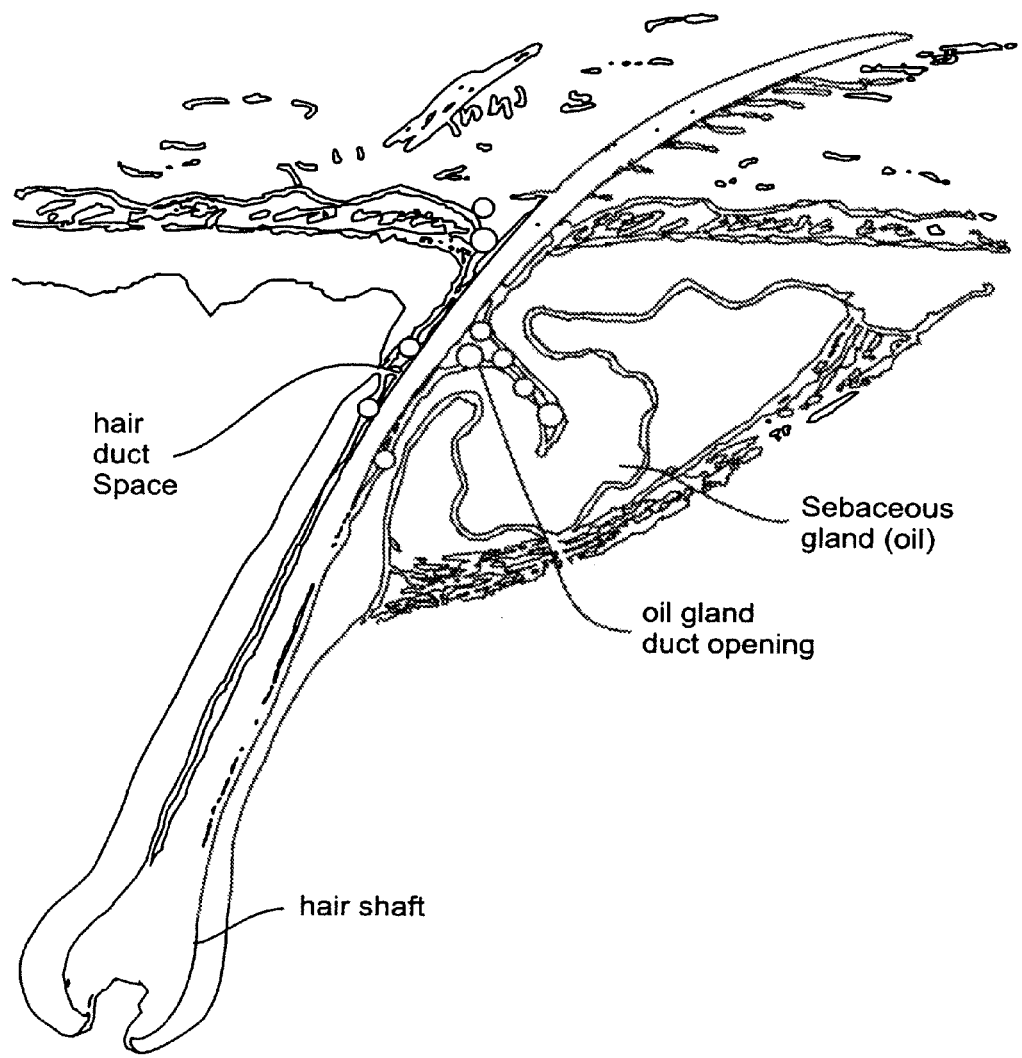
FIG. 2 illustrates, in an enlarged view, an example of a distribution of particles having an average diameter of about five microns in a hair duct and sebaceous glands.
Figure 3:
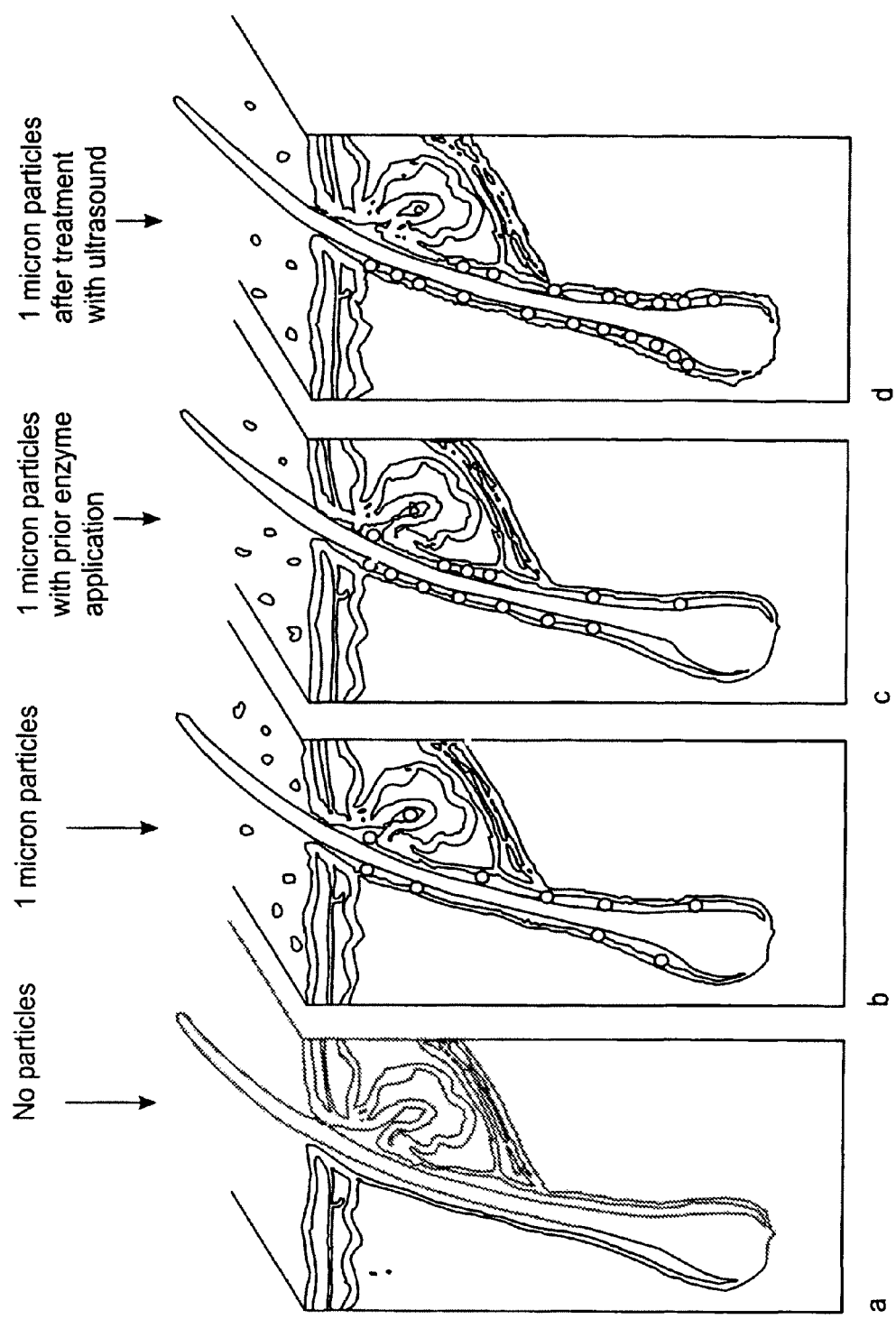
FIG. 3a illustrates an example of a hair duct and sebaceous glands without any particles being present.
FIG. 3b illustrates an example of a distribution of particles having an average diameter of about one micron in a hair duct and sebaceous glands
FIG. 3c illustrates an example of a distribution of particles having an average diameter of about one micron in a hair duct and sebaceous glands in which an enzyme has been used to help "unplugs" hair follicle openings, thus allowing more particles to penetrate.
FIG. 3d illustrates an example of a distribution of particles having an average diameter of about one micron in a hair duct and sebaceous glands in which ultrasound treatment has been used to increase the number of particles in the hair duct and enabled the particles to penetrate the deeper part of the hair duct.
Figure 4:
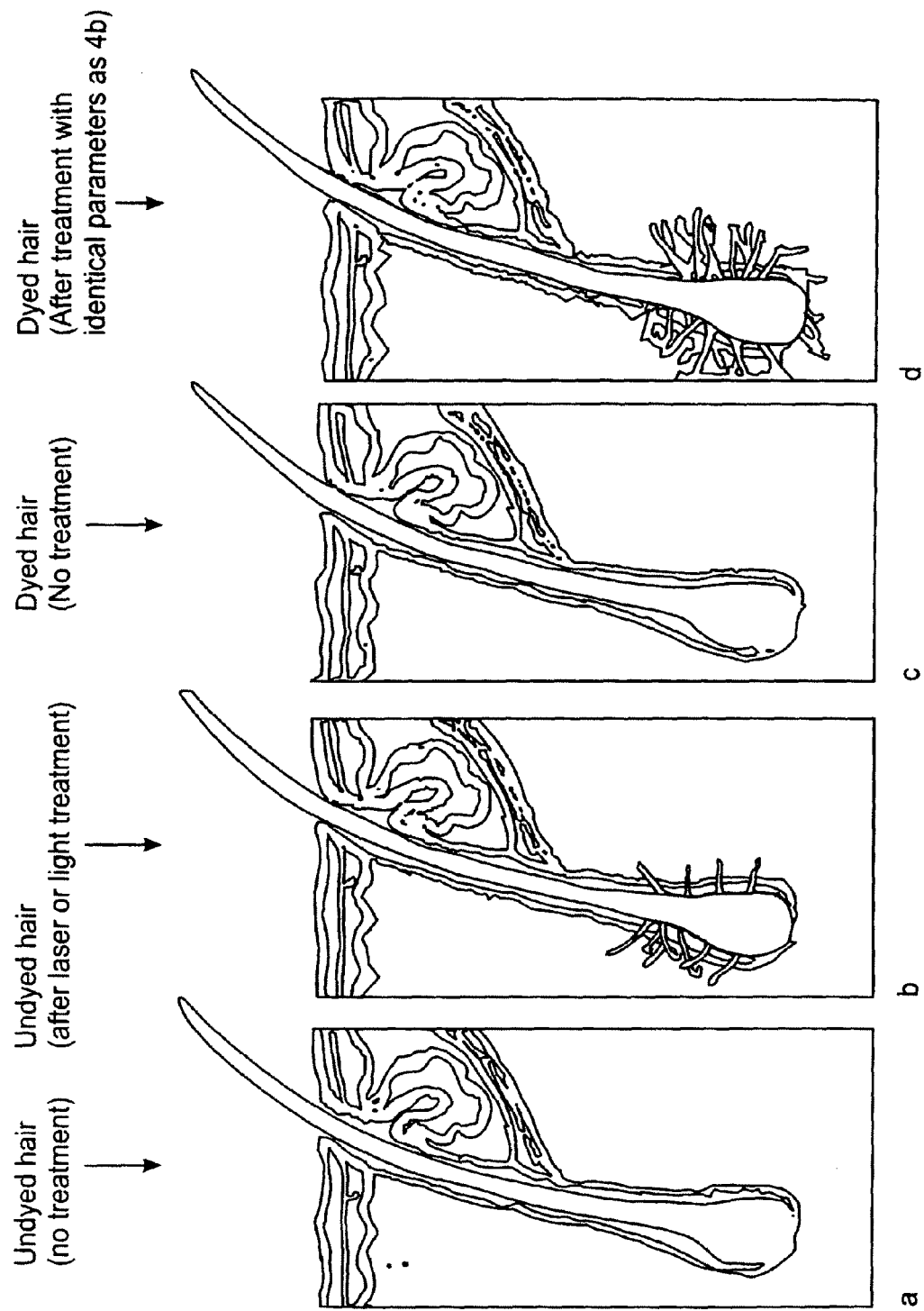
FIG. 4a illustrates an example of a hair duct and sebaceous glands prior to hair dying treatment.
FIG. 4b illustrates an example of a hair duct and sebaceous glands prior to hair dying treatment and after laser or light treatment.
FIG. 4c illustrates an example of a hair duct and sebaceous glands after hair dying treatment.
FIG. 4d illustrates an example of a hair duct and sebaceous glands after hair dying treatment and after laser or light treatment using parameters substantially identical to those used in the example illustrated in FIG. 4b. The example illustrated in FIG. 4b shows less damage than the example illustrated in FIG. 4d after otherwise identical treatment.
Figure 5:
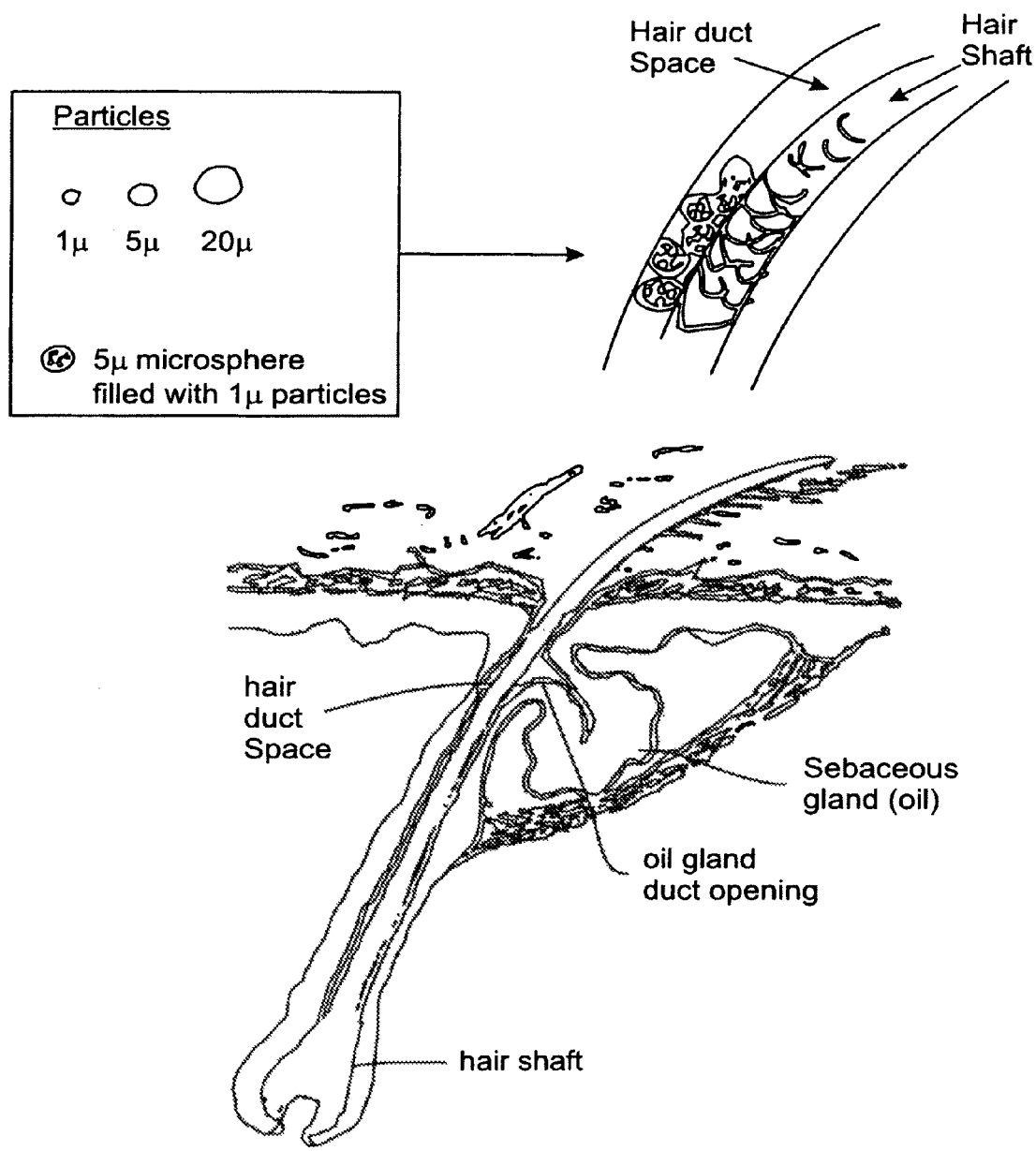
FIG. 5 illustrates, in an enlarged view, an example of a distribution of particles having an average diameter of about one micron encapsulated in microspheres having an average diameter of about five microns in a hair duct and sebaceous glands.

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, the present invention is directed to a process for producing temporary or permanent reduction or removal, in human or mammalian skin, of some or all of the hairs growing in hair follicles and exiting the skin through hair ducts. In a preferred embodiment the process produces little or no permanent injury or damage to nearby skin tissue. Substantially only the hair follicle and immediately surrounding tissue are damaged.

In a process according to one embodiment of the present invention, an agent may be selected which is capable of penetrating the hair ducts and attaching, bonding or otherwise becoming incorporated into the hair shaft, hair follicle, hair bulb or hair duct cells. The agent may be characterized as an active agent in that it performs a function in addition to simply occupying or contaminating the space in the ducts surrounding the hair shaft. The agent may have sufficient optical absorption of a wavelength (or a combination of wavelengths) of a coherent or non-coherent light source which can penetrate the skin adequately to be absorbed by the target agent or the new agent-tissue complex.

The area of skin from which unwanted hair is to be removed may be cleansed. After the skin is cleansed, the hair and/or the skin may be treated to improve permeability. This may be accomplished, for example, by treating the hair and/or skin with steam or a hot moist towel to hydrate the skin and hair.

The agent may be applied in sufficient quantity and in suitable form to be incorporated into the target tissue in adequate or optimal amounts to allow the production of the desired tissue effect.

Excess agent may be removed, neutralized, inactivated, decolorized, diluted or otherwise altered so that residual contamination of the skin or hair duct space by such excess agent is either (a) absent and does not interact with the light or energy source, or (b) present in such small quantity that it provides no clinical effect.

Delivery of the desired agent into the target tissues may be enhanced, facilitated or made possible by the use of enzymes or by the use of ultrasound or phonophoresis either for penetration into the hair duct or the hair follicle or hair bulb cells or to penetrate into the hair shaft itself or surrounding target tissues or to cause the release of the agent from the encapsulated delivery device such as liposomes, polymers, microspheres, etc. so as to cause penetration or attachment of this active agent. The water content or absorption by the hair shaft might be enhanced, to increase the hair shaft diameter and volume or to otherwise enhance the process.

Ultrasound may be used therapeutically to interact directly with the agent or the agent-tissue complex to produce the desired damaged target tissues (to be used alone or in combination with laser or non-laser light sources). Ultrasound may be used to make graphite penetrate better, for example. A more detailed description of several aspects of the use of ultrasound may be found, for example, in the applicant's co-pending U.S. patent application Ser. No. 09/087,146 for "Ultrasound Enhancement of Percutaneous Drug Absorption."

Although preferred embodiments of the present invention may use ultrasound and/or laser or light energy, the present invention is not limited to the use of these energy sources. Other sources of energy, including (without limitation) microwave energy and radio frequency energy may also be used.

The targeted skin may be exposed to one or more wavelengths of laser or non-laser light or single or multiple frequencies of ultrasound. A variety of parameters may be used (including pulse duration, energy, single or multiple pulses, the interval between pulses, the total number of pulses, etc.) to deliver sufficient cumulative energy to interact with the agent or tissue complex. This may result in injury, damage or destruction of the hair follicle, hair bulb or the supporting skin tissue, thereby delaying regrowth of the hairs, or diminishing the hair shaft diameter, or miniaturizing the hair follicles or completely destroying these tissues, resulting in permanent hair removal. Ultrasound may also be used to preheat the target structures, the skin, and/or the hair.

The agent may be incorporated into the target tissue'by a variety of mechanisms. These mechanisms include, but are not limited to: 1) physical incorporation into the hair shaft or target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation: hair dyes, vegetable dyes, food coloring, fabric dyes, tissue stains, shoe or leather dyes, other plant products (such as flavonols, chlorophyll, carotenoids, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to melanin in the hair shaft or surrounding follicle, bulge or duct cells directly, whether by topical or systemic agents that localize in the target tissues.

Agents may be delivered in pure form, in solution, in suspension, in emulsions, in liposomes, in synthetic or natural microspheres, microsponges or other known microencapsulation vehicles.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent.

One preferred embodiment uses a hair dye incorporated into the hair shafts. The dye may be selected to absorb 1064 nm laser light. Depending upon the wavelength of laser light, suitable hair dyes may include, for example, Professional Miss Clairol 52D Black Azure or 51D Black Velvet. Laser pulse durations may be selected with sufficient power density to allow the target tissue to be appropriately damaged.

One known hair removal process uses a solution of graphite in oil lotion and a Q-switched 1064 nm Nd:YAG laser. The solution may be applied to the skin and hair and then the skin and hair may be treated with the laser using known parameters. It may be preferable to use a high repetition rate, such as 8-10 Hertz or higher, and move the laser handpiece slowly enough that pulses are "stacked" in one spot for several pulses before the handpiece is moved to an adjacent spot. It has been found that there is a stair-step like effect of incremental temperature rise in the dyed hairs with the second and third pulses versus a single pulse. A faster repetition rate also tends to help build the heat up faster, and to higher levels. This tends to produce the maximum heat (which is desirable, as long as the heat stays confined to the hair follicle and the immediately adjacent supporting tissues). Since this effect occurs substantially simultaneously with other destructive effects of the process, the damage to hair growth tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate. Safety remains at about the same level, since dye related damage tends to be confined to target tissues. There is no appreciable change in treatment time.

In an alternative embodiment, a hair dying process similar to that described above may be used with a laser that tends to target melanin rather than graphite contaminant. Such a laser may be, for example, a long pulsed alexandrite or long pulsed ruby or diode laser. In the case of a long pulsed alexandrite laser, tests have been conducted using a Cynosure LPIR version at 755 nm wavelength and 20 J/cm2 and 20 msec pulse duration with a dye that absorbs at 755 nm. Infrared camera analysis of hair treated according to this process shows both relatively higher temperature and also relatively slower cooling of the hair shafts themselves. This allows further heating of the target tissues. It also helps make'the treatment safer and probably more effective.

Another preferred embodiment uses a longer pulsed laser in the 750 nm-1000 nm range and appropriate parameters to achieve the desired tissue damage goal.

Another embodiment uses a tissue dye which attaches to, or is incorporated into, a target cell and surrounding tissues. The target tissue may be illuminated with a multi-wavelength non-laser light source using appropriate parameters to achieve the desired tissue damage goal.

Another embodiment uses a light source which is well-absorbed by the melanin naturally present in undyed darker hairs and a hair dye which may be incorporated into the hair shaft. The hair dye will be well-absorbed by the same wavelength of light (or alternatively two or more wavelengths, one for melanin and one or more for the dye) which is absorbed by the undyed hair, resulting in an enhanced or greater injury to the target tissue (or permitting lower treatment energy parameters, resulting in safer treatment than if the hairs were treated without the hair dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the native hair pigment and also by the hair dye used. A pulse duration on the order of between about one and thirty seconds appears to be preferable. This also tends to be a much longer time than is used in most systems in use today.

Another embodiment uses an agent which facilitates cavitation shock waves or a thermal effect, or both. This preferentially damages (or stimulates) the target tissues while minimizing damage (or other adverse effects) on surrounding non-target tissues. This may be used with very short pulsed lasers or light sources or with ultrasound alone.

In one embodiment a process in accordance with the present invention may be used to temporarily or permanently stimulate hair growth in human or mammalian skin. Some or all of the hair follicles in the treatment area may be stimulated to grow, to have their growth cycle accelerated, to prolong the hair growth cycle, to increase the hair shaft diameter, to change the hair shaft color, to stimulate hairs that are in a dormant state or which originate from an area of hair loss or baldness, or to produce a combination of the above-mentioned effects. This tends to involve a lower level of delivered energy than that used for hair reduction. Phonophoresis may be used to deliver other stimulating or growth supporting agents.

In one embodiment a process in accordance with the present invention may be used to provide short or long-term control, improvement, reduction or elimination of acne or other skin diseases. An active agent may be physically or chemically or immunologically incorporated into cells of the sebaceous (oil) glands or into the naturally occurring acne bacteria, yeast or similar organisms which feed on the oil in the oil glands (or sweat glands)or are otherwise relatively benign inhabitants. Improvement in skin disorders may be a direct or indirect result of the application of the agents in this process, as may reduced oiliness of the skin, reduced size or diminished appearance of pores, etc.

Other similar disorders such as folliculitis which involve the pilo-sebaceous (hair/oil gland) unit may also be treated using the present invention. The present invention may also be used to reduce perspiration, sweating, or hyperhidrosis from eccrine (sweat) glands or apocrine glands. A preferred embodiment of the present invention may be used to treat other skin disorders such as, for example, viral warts, psoriasis, precancerous solar keratosis or skin lesions, hyperhidrosis/excessive sweating, and perhaps skin ulcers(diabetic, pressure, venous stasis).

A preferred embodiment of the present invention may use various microencapsulation processes to deliver active agents. If the diameter of the micro encapsulations is about five microns, then there may be relatively site specific preferential delivery into the sebaceous oil glands or skin surface stratum corneum cells. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. The micro encapsulations may be synthetic or natural. If ultrasound is used to enhance penetration, then the diameters and ultrasound treatment parameters may need to be adjusted according to the applicable principles which allo the estimation of the optimal ultrasound parameters for driving small particles into the skin, skin appendages or skin orifices.

Microencapsulation may be used to improve delivery of known agents such as indocyanine green and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the sebaceous gland and/or hair.

Indocyanine green dye is presently in medical use, appears to be relatively benign, may be activated by red visible lasers (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference.

The microsponges containing the active agent may selectively attach, or at least have a chemical affinity for, some part of the oil gland. The ICN dye may be conjugated with lipids, which would then have an affinity for the oil glands. Alternatively, the attachment may occur after the active agent is released from the microsponge, either passively or by attractive or chemical forces. In the case of some microencapsulation carrier vehicles, release may occur after disruption of the vehicle integrity itself, possibly by ultrasound or laser or light or other energy source or perhaps a chemical reaction.

In a preferred embodiment the ICN dye may be mixed with lipids, or put into microsponges (a.k.a. microspheres), and then applied to the skin surface, allowed to sit for a time. Excess dye may be removed, and then the area may be treated with laser light at about 800 nm, between about 0.1 and 100 millisec pulses and around 1.0-10.0 Joules/cm$^2$.

U.S. Pat. No. 5,817,089 specifies "particles having a major diameter of about 1 micron". It has been discovered, however, that these diameters may not be optimal. A 1993 Pharmaceutical Research journal article by Rolland et al describes an acne treatment wherein a topical acne drug is delivered with less irritation by putting the drug into synthetic polymer microsphere sponges. This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices". In a preferred embodiment for treatment of acne, graphite particles having an average diameter of about one micron may be placed in delivery devices, such as microsponges, having an average diameter of about five microns. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to sweat glands may be improved.

Use of such applications could enable selective delivery of anti-acne agents, or hair dye for laser hair removal, or agents which stimulate hair growth, or other hair treatments, where the encapsulation diameter was used, with or without ultrasound, to preferentially deliver, and ultrasound at different parameters or laser was used to release (not necessarily to activate or interact).

These techniques may be applied to many other agents in addition to ICN dye and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, the sebaceous oil glands, or other structures. Air pressure or other gases or liquids may be used to enhance delivery or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells, or (2) the use of ultrasound to drive graphite particles into spaces between the stratum corneum to enhance the effects of a skin peel process (which physically removes a portion of the outer layers of the skin surface).

A known skin peel process may be improved by using ultrasound to open intercellular spaces in the outer stratum corneum layer of the skin via cavitation. Then a graphite lotion may be driven in further with the same or similar ultrasound. Fibroblast stimulation may be optimized with both topical agents that are applied afterwards (while the skin is still relatively permeable) and also with additional low level laser stimulation.

The processes described above may be used to deliver two different agents, either serially or simultaneously. The two agents may then be activated by the laser together to work synergistically, or to combine and then have an effect, or to deliver two different agents that may be activated simultaneously or very closely in time.

Two entirely different laser or light beams may be delivered substantially simultaneously through the same optics at different parameters. For example, one beam may be delivered primarily to release or to activate, and a second beam primarily to treat. Additive effects may be achieved by using two beams at the same time. For example, a known process for skin peel and hair reduction may be optimal at 1064 nm for safety and for treating all skin colors, but other wavelengths may be better to achieve a low level laser stimulation of fibroblasts. The same laser handpiece may deliver the known process for skin peel and hair reduction, and either simultaneous or synchronized sequentially in time deliver another wavelength that may be optimal to complement. In the one case it may be the best wavelength to stimulate fibroblasts. In another case it may allow selection of a hair dye (or other agent) having very strong affinity for hair and very strong absorption.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A process for the treatment of psoriasis affecting mammalian skin, comprising:
    selecting at least one photoactive agent, the agent having an electromagnetic radiation absorption characteristic enabling the agent to absorb at least a first wavelength of electromagnetic radiation from an electromagnetic radiation source,
    applying the agent to at least a portion of the mammalian skin affected by psoriasis, and
    exposing the agent substantially simultaneously to electromagnetic radiation from at least a first source of electromagnetic radiation comprising at least the first wavelength of electromagnetic radiation to activate the agent and to electromagnetic radiation comprising at least a second wavelength of electromagnetic radiation from a second source to treat the psoriasis, whereby the agent absorbs the first wavelength of electromagnetic radiation.

2. The process of claim 1, wherein the electromagnetic radiation source produces an energy fluence of from about 1.0 $J/cm^2$ to about 10 $J/cm^2$.

3. The process of claim 1, comprising exposing the agent to ultrasound.

4. The process of claim 1, wherein the electromagnetic radiation source is at least one light emitting diode.

5. The process of claim 1, comprising exposing the agent to the first wavelength of electromagnetic radiation and to the second wavelength of electromagnetic radiation through the same optics.

6. The process of claim 1, wherein the second source of electromagnetic radiation provides the second wavelength of electromagnetic radiation.

* * * * *